United States Patent [19]
Holtz et al.

[11] Patent Number: 5,231,178
[45] Date of Patent: Jul. 27, 1993

[54] METHOD FOR THE PURIFICATION OF INTACT, CORRECTLY-FOLDED INSULIN-LIKE GROWTH FACTOR-1

[75] Inventors: Gregory C. Holtz; Russell A. Brierley, both of San Diego, Calif.

[73] Assignee: The Salk Institute Biotechnology/Industrial Associates, Inc., La Jolla, Calif.

[21] Appl. No.: 785,171

[22] Filed: Oct. 28, 1991

Related U.S. Application Data

[63] Continuation-in-part of Ser. No. 641,430, Jan. 16, 1991, abandoned.

[51] Int. Cl.$^5$ .................... C12N 15/18; C07K 7/10; A61K 37/36
[52] U.S. Cl. ................................. 530/399; 435/69.4
[58] Field of Search .................. 530/399; 514/12; 435/69.4

[56] References Cited

U.S. PATENT DOCUMENTS 4,769,361 9/1988 Burleigh et al. .................. 514/12
4,963,665 10/1990 Rotwein et al. .................. 530/399
4,997,916 3/1991 Aviv et al. .................. 435/69.4

FOREIGN PATENT DOCUMENTS 0360411 3/1990 European Pat. Off. .

OTHER PUBLICATIONS

Protein Purification = Principles and Practice (1982), p. 140, Scopes.
Baxter, et al. "Natural and Recombinant DNA-derived Human Insulin-Like Growth Factor-I Compared for Use In Radioligand Assays", Chemical Abstracts, 107, p. 86 (1987); Abstract No. 33292.
Wang, et al., "Purification and Assay of Insulin-Like Growth Factor-Binding Protein-1; Measurement of Circulating Levels Throughout Pregnancy", J. of Endocrinology 128, pp. 161-168 (Jan. 1991).
Armstrong, et al., "Biological Activity of Insulin-Like Growth Factor-1 Purified from Chicken Serum", Domestic Animal Endocrinology, 7(3): 383-393 (1990).
Elliott, et al., "Yeast-Derived Recombinant Human Insulin-Like Growth Factor I: Production, Purification, and Structural Characterization," J. Prot. Chem. 9, pp. 95-104 (1990).
Gellerfors, et al., "Isolation and Characterization of a Glycosylated Form of Human Insulin-Like Growth Factor I Produced in Saccharomyces Cerevisiae*", J. Biol. Chem. 264, pp. 11444-11449 (1989).
"Superdex 75 HR 10/30 High Performance Gel Filtration Column" Pharmacia LKB Biotechnology Publication SUDF 50-01-524.
Peters, et al., "Expression of a Biologically Active Analogue of Somatomedin-C/Insulin-like Growth Factor I", Gene 35, pp. 83-89 (1985).
Bayne, et al., "Expression, Purification and Characterization of Recombinant Human Insulin-like Growth Factor I in Yeast", Gene 66, pp. 235-244 (1988).
Nilsson, et al., "Efficient Secretion and Purification of Human Insulin-like Growth Factor I with a Gene Fusion Vector in *Staphylococci*," Nucl. Acids. Res. 13, pp. 1151-1163 (1985).
Ray, et al., "Use of High-Performance Liquid Chromatography in the Purification of Human Somatomedin-C", Biochem. Soc. Trans. 13, pp. 1233-1234 (1985).
Chernausek, et al., "Efficient Purification of
(List continued on next page.)

*Primary Examiner*—Howard F. Schain
*Attorney, Agent, or Firm*—Fitch, Even, Tabin & Flannery

[57] ABSTRACT

Method for the recovery and purification of intact, correctly-folded, monomeric insulin-like growth factor-1 peptide from large volumes of IGF-1-containing medium are described, comprising a series of adsorption-desorption steps employing a combination of cation exchange and hydrophobic interaction adsorbents. Product IGF-1 peptide is highly purified and suitable for use in a variety of clinical applications.

56 Claims, 1 Drawing Sheet

OTHER PUBLICATIONS

Somatomedin-C/Insulin-like Growth Factor I Using Immunoaffinity Chromatography", Biochem. Biophys. Res. Comm. 126, pp. 282-288 (1985).

Petrides, et al., "An Improved Method for the Purification of Human Insulin-Like Growth Factors I and II*", Endocrinology 118, pp. 2034-2038 (1986).

Pfeifle, et al., "Insulin-Like Growth Factor I/Somatomedin-C: A Rapid Isolation Procedure with FPLC", Prep. Biochem. 15(5), pp. 291-307 (1985).

Rubin, et al., "Isolation and Partial Sequence Analysis of Rat Basic Somatomedin*", Endocrinology 110, pp. 734-740 (1982).

Cornell, et al., "Isolation of Insulin-Like Growth Factors I and II from Human Plasma", Prep. Biochem. 14(2), pp. 123-138 (1984).

Svoboda, et al., "Purification of Somatomedin-C from Human Plasma: Chemical and Biological Properties, Partial Sequence Analysis, and Relationship to Other Somatomedins", Biochemistry 19, pp. 790-797 (1980).

Meng, et al., "Reduction Studies on Bacterial Recombinant Somatomedin C Insulin-Like Factor14 1", J. of Chromatography 443, pp. 183-192 (1988).

METHOD FOR THE PURIFICATION OF INTACT, CORRECTLY-FOLDED INSULIN-LIKE GROWTH FACTOR-1

This is a continuation-in-part of application Ser. No. 07/641,430, filed Jan. 16, 1991, now abandoned.

This invention relates to purification methods. In a particular aspect, this invention relates to the purification of insulin-like growth factor-1 peptides from fluid medium containing same. In one aspect, the present invention relates to methods for purification of insulin-like growth factor-1 peptides produced by recombinant techniques. In another aspect, the present invention relates to methods for the purification of insulin-like growth factor-1 peptides produced by yeast cells transformed with at least one copy of a DNA sequence encoding an insulin-like growth factor-1 peptide.

BACKGROUND OF THE INVENTION

Insulin-like growth factor-1 (IGF-1) is a polypeptide of 70 amino acids with a molecular weight of 7648 daltons. This single chain protein has three intrachain disulfide bridges. These disulfide bonds, along with numerous hydrogen bonds and hydrophilic interactions, maintain the compact tertiary structure of this molecule. However, it has been shown that, upon reduction and reoxidation, IGF-1 can refold in a variety of ways, forming as many as 15 monomeric configurations [see Meng, et al., *J. Chrom.* 433:183 (1988)]. Consequently, attempts to produce large quantities of this peptide can lead to the formation of a complicated mixture of product forms which must be purified for further use.

Insulin-like growth factor-1 belongs to a heterogeneous family of peptides which share some of the biological and chemical properties of insulin, but which are antigenically distinct from insulin. Currently available experimental evidence suggests that IGF-1 promotes growth by mediating the effects of growth hormone. Thus, such processes as skeletal growth, cell replication and other growth related processes are affected by IGF-1 levels. Physiological concentrations of IGF-1 have been shown to be influenced by such conditions as thyroid disease, diabetes and malnutrition [see Preece, in *Horm. Blood*, 4: 108 (1983)].

IGF-1 has also been shown to act synergistically with other growth factors, for example, in accelerating the healing of soft and mesenchymal tissue wounds [see Lynch et al., in *J. Clin. Periodontol.*, 16: 545 (1989) and Lynch et al., in *Proc. Natl. Acad. Sci. USA*, 84: 7696 (1987)], and in enhancing the growth of mammalian cells in serum-free tissue culture medium [see Burleigh and Meng, in *American Biotech. Lab.*, 4: 48 (1986)].

Considering the many clinical and research applications of IGF-1, a ready supply of IGF-1 will be of great value to the medical and biotechnology fields. Since isolation from natural sources is technically difficult, expensive, and time consuming, recent efforts have centered on the development of efficient recombinant methods for the production of IGF-1.

The methylotrophic yeast *Pichia pastoris* has recently been developed as an improved host for the production of recombinant products. Recombinant *Pichia pastoris* strains have been shown to be capable of secreting certain recombinant proteins in the gram per liter range. In addition, such strains have been shown to be capable of adapting to fed batch or continuous cultivation fermentation conditions. Moreover, such strains have an extremely stable recombinant phenotype and are capable of maintaining high yields of the desired recombinant expression product over several orders of fermentation scale. Indeed, Brierley, et al., in copending application U.S. Ser. No. 578,728, filed Sep. 4, 1990, have recently shown that *P. pastoris* is an excellent host for the recombinant production of IGF-1. The disclosure of this copending application is hereby incorporated by reference in its entirety. In view of the availability of medium containing high levels of recombinantly produced IGF-1, there is needed an efficient means for the recovery and purification of IGF-1 from such medium.

Recombinantly produced IGF-1 frequently consists of a mixture of several different forms of IGF-1, i.e., intact, monomeric, correctly-folded material (also referred to herein as authentic IGF-1), as well as various aberrant forms, such as, misfolded material (i.e., having improperly formed disulfide bonds), nicked material (i.e., wherein one or more of the peptide bonds of the amino acid backbone have been broken, but the molecular weight of the resulting species is substantially the same as that of intact material, since the nicked material has the same number of amino acid residues as intact material, and the fragments of nicked material are held together by disulfide bonds), cleaved material (e.g., wherein one or more peptide bonds are broken so that two fragments of lower molecular weight, relative to intact material, are produced; or peptide lacking one or more amino acid residues relative to intact material), multimeric forms (i.e., dimers, trimers, etc., wherein disulfide bonds are formed between two or more different IGF-1 monomer chains), and so on. Due to the substantial similarity of the various forms of IGF-1, the purification of recombinantly produced material presents a difficult technical challenge. Not only does such purification require the separation of IGF-1 peptides from the other peptides produced during fermentation, in addition, a separation is required which is selective enough to distinguish between the various forms of IGF-1 which may be present.

Brierley et al. also describe in co-owned international application No. PCT/US91/06452, which is a continuation-in-part of U.S. Ser. No. 578,728 filed with the Patent Cooperation Treaty on Sep. 4, 1991, production of IGF-1 in *P. pastoris* strains deficient in proteolytic activities that can degrade the recombinant product to yield aberrant forms such as nicked IGF-1. The use of protease-deficient strains of *P. pastoris* as hosts for recombinant expression of heterologous proteins susceptible to degradation by *P. pastoris* proteases is described in U.S. Ser. No. 07/678,916 filed Apr. 1, 1991. The disclosure of these co-pending applications is hereby incorporated by reference in their entirety. Fermentations of IGF-1-producing *P. pastoris* strains deficient in proteolytic activity yielded 50–100% more authentic IGF-1 and 30% less nicked IGF-1 than similar fermentations of IGF-1-producing *P. pastoris* strains that were not deficient in proteolytic activity. Although purification of authentic IGF-1 from the broth of a *P. pastoris* strain deficient in proteolytic activity might be facilitated by the lower amounts of nicked IGF-1 in the broth, a separation process capable of distinguishing between the various forms of IGF-1 is still required for such purification

SUMMARY OF THE INVENTION

In accordance with the present invention, we have developed an efficient method for the recovery and purification of IGF-1 peptides from fluid medium containing same. The invention method involves successive selective adsorption-desorption steps on a combination of cation exchange and hydrophobic interaction chromatography matrix materials and may preferably include gel filtration chromatography. In this way, about 30-50% recovery of substantially purified, intact, correctly-folded, monomeric IGF-1 can be accomplished in the presence of various other forms of IGF-1 which are initially present in the crude IGF-1 containing medium.

DETAILED DESCRIPTION OF THE INVENTION

Figure 1:
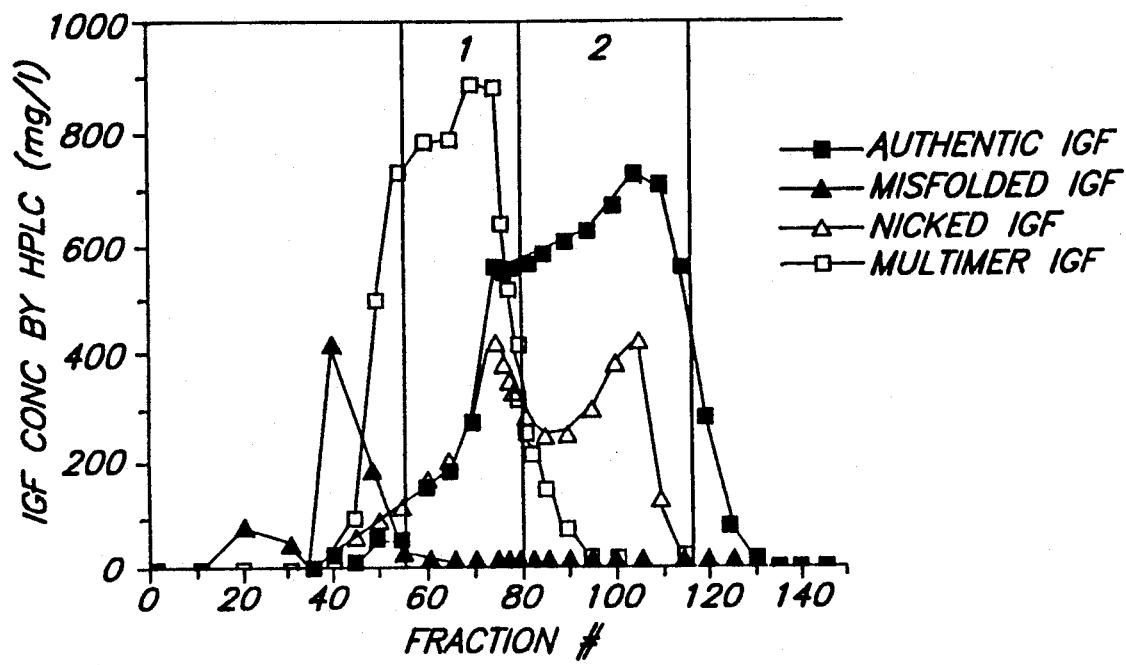
FIG. 1 is an elution profile for elution of various IGF-1 species from the first hydrophobic interaction chromatography matrix.

In one aspect, the present invention entails a method for the purification of monomeric intact, correctly-folded insulin-like growth factor-1 peptide (IGF-1) from medium containing IGF-1 peptides, said method comprising:

(a) contacting said medium with a sufficient quantity of first cation exchange material under conditions suitable to adsorb at least about 95% of total IGF-1 from said medium, (b) eluting the adsorbed IGF-1 from the IGF-1-containing cation exchange material of step (a) by contacting said cation exchange material with a sufficient quantity of a solvent system which has a sufficiently high pH or ionic strength so as to displace substantially all of said IGF-1 from said cation exchange material, (c) contacting the IGF-1-containing fractions of the eluate of step (b), in a suitable solvent system, with a sufficient quantity of a first hydrophobic interaction chromatography matrix under conditions suitable to adsorb in the range of about 95 up to 100% of said IGF-1 from said eluate, (d) eluting the adsorbed IGF-1 from said first hydrophobic interaction chromatography matrix by contacting said matrix first with in the range of about 1 up to 10 volumes, relative to the volume of matrix, of a buffer system having a sufficiently low conductivity so as to displace aberrant IGF-1 peptides from said matrix, without displacing significant quantities of the intact, monomeric, correctly-folded form of adsorbed IGF-1 from said first hydrophobic interaction chromatography matrix, followed by contacting said matrix with in the range of about 1 up to 10 volumes, relative to the volume of matrix, of a buffer system having an elevated pH, wherein said elevated pH is sufficiently high so as to displace substantially all of the remaining adsorbed forms of IGF-1 from said matrix.

In accordance with another of its aspects, the present invention entails a method for the purification of monomeric intact, correctly-folded insulin-like growth factor-1 peptide (IGF-1) from medium containing IGF-1 peptides, said method comprising:

(a) contacting said medium with a sufficient quantity of first cation exchange material under conditions suitable to adsorb at least about 95% of total IGF-1 from said medium, (b) eluting the adsorbed IGF-1 from the IGF-1-containing cation exchange material of step (a) by contacting said cation exchange material with a sufficient quantity of a solvent system which has a sufficiently high pH or ionic strength so as to displace substantially all of said IGF-1 from said cation exchange material, (c) contacting the IGF-1-containing fractions of the eluate of step (b), in a suitable solvent system, with a sufficient quantity of a first hydrophobic interaction chromatography matrix under conditions suitable to adsorb in the range of about 95 up to 100% of said IGF-1 from said eluate, (d) eluting the adsorbed IGF-1 from said first hydrophobic interaction chromatography matrix by contacting said matrix first with in the range of about 1 up to 10 volumes, relative to the volume of matrix, of a buffer system having a sufficiently low conductivity so as to displace aberrant IGF-1 peptides from said matrix, without displacing significant quantities of the intact, monomeric, correctly-folded form of adsorbed IGF-1 from said first hydrophobic interaction chromatography matrix, followed by contacting said matrix with in the range of about 1 up to 10 volumes, relative to the volume of matrix, of a buffer system having an elevated pH, wherein said elevated pH is sufficiently high so as to displace substantially all of the remaining adsorbed forms of IGF-1 from said matrix;

(e) contacting the intact, momomeric, correctly-folded IGF-1-containing fractions of the eluate from step (d), in a suitable solvent system, with a sufficient quantity of a gel filtration chromatography matrix having suitable pore size to effect resolution of the intact, monomeric correctly-folded form of IGF-1 from substantially all multimeric forms of IGF-1; and (f) eluting said gel filtration chromatography matrix with a sufficient quantity of an eluent so as to cause the intact, monomeric correctly-folded form of IGF-1 to be resolved from said multimeric forms of IGF-1.

In accordance with the present invention, there is provided a method for the purification of monomeric, intact, correctly-folded insulin-like growth factor-1 peptide (IGF-1) from medium containing IGF-1 peptides, said method comprising:

(a) contacting said medium with a sufficient quantity of first cation exchange matrix under conditions suitable to adsorb at least about 95% of total IGF-1 from said medium, (b) eluting the adsorbed IGF-1 from the IGF-1-containing cation exchange matrix of step (a) by contacting said cation exchange matrix with a sufficient quantity of a solvent system which has a sufficiently high pH or ionic strength so as to displace substantially all of said IGF-1 from said cation exchange material, (c) contacting the IGF-1-containing fractions of the eluate of step (b), in a suitable solvent system, with a sufficient quantity of a first hydrophobic interaction chromatography matrix under conditions suitable to adsorb in the range of about 95 up to 100% of said IGF-1 from said eluate, (d) eluting the adsorbed IGF-1 from said first hydrophobic interaction chromatography matrix by contacting said matrix first with in the range of about 1 up to 10 volumes, relative to the volume of resin, of a buffer system having a sufficiently low conductivity so as to displace some of the aberrant IGF-1 peptides from said matrix, without displacing significant quantities of the intact, monomeric, correctly-folded form of adsorbed IGF-1 from said first hydrophobic interaction chromatography matrix, followed by contacting said matrix with in the range of about 1 up to 10 volumes, relative to the volume of matrix, of a buffer system having an elevated pH, wherein said elevated pH is sufficiently high so as to displace substantially all of the remaining adsorbed forms of IGF-1 from said matrix, (e) contacting the fractions eluted according to step (d) employing said buffer system having an elevated pH which contain, as the predominant form of IGF-1, intact, monomeric, correctly-folded IGF-1, wherein said contacting is carried out with a sufficient quantity of a second cation exchange matrix under conditions suitable to adsorb in the range of about 95 up to 100% of total IGF-1 from said eluate, (f) eluting the adsorbed IGF-1 from said second cation exchange matrix by contacting said matrix with at least one volume, relative to the volume of matrix, of a buffer system having a sufficient ionic strength so as to differentially displace substantially all of the IGF-1 peptides from said matrix, (g) contacting the intact, monomeric, correctly-folded IGF-1-containing fractions of the eluate from step (f), in a suitable solvent system, with either (1) a sufficient quantity of a second hydrophobic interaction chromatography matrix under conditions suitable to adsorb in the range of about 95 up to 100% of all forms of IGF-1 from said eluate, or (2) a sufficient quantity of a gel filtration matrix having suitable pore size to effect resolution of the intact, monomeric, correctly folded form of IGF-1 from substantially all multimeric forms of IGF-1 and, (h) (1) after step (g) (1), eluting adsorbed IGF-1 from said second hydrophobic interaction chromatography matrix by contacting said matrix first with in the range of about 1 up to 10 volumes, relative to the volume of matrix, of a buffer system having a sufficiently low conductivity so as to displace substantially all forms of IGF-1 other than the intact, monomeric, correctly-folded form of IGF-1 from said matrix, without displacing significant quantities of the intact, monomeric, correctly-folded form of adsorbed IGF-1, followed by contacting said matrix with in the range of about 1 up to 10 volumes, relative to the volume of matrix, of a buffer system having a sufficiently high pH so as to displace substantially all of the remaining adsorbed IGF-1 from said matrix or (2) after step (g) (2), eluting said gel filtration chromatography matrix with a sufficient quantity of elution buffer as to cause the intact, monomeric, correctly-folded form of IGF-1 to be resolved from said multimeric forms of IGF-1.

In accordance with a specific embodiment of the present invention, there is provided a method for the purification of monomeric, intact, correctly-folded insulin-like growth factor-1 (IGF-1) peptide from medium containing IGF-1 peptides, wherein said medium containing IGF-1 is the substantially cell-free fermentation broth from a high cell density yeast fermentation operation, and wherein said yeast are transformed with at least one DNA fragment comprising, in the direction of transcription, the following DNA sequences:

(i) a promoter region of a methanol responsive gene of *P. pastoris*, (ii) a DNA sequence encoding a polypeptide consisting of:

(a) the *S. cerevisiae* alpha mating factor (AMF) prepro sequence, including a processing site selected from the group consisting of lys-arg; and lys-arg-(glu-ala)$_x$, wherein x is an integer between 1 and about 3, and (b) an insulin-like growth factor-1 (IGF-1) peptide; and (iii) a transcription terminator functional in *P. pastoris*, wherein said DNA sequences are operationally associated with one another for transcription of the sequences encoding said polypeptide, said method comprising:

(a) contacting said medium with a sufficient quantity of a sulfylpropylated cation exchange media under conditions suitable to adsorb at least about 95% of said IGF-1 from said medium; wherein at least 0.03 liters, per gram of IGF-1 in said medium, of said cation exchange material are employed; and wherein said contacting is carried out at a temperature in the range of about 2° up to 30° C., and wherein, optionally, the IGF-1-containing media may be diluted prior to contacting with the cation exchange material with a low conductivity buffered medium having the same pH as the medium used to equilibrate the cation exchange material, (b) contacting the IGF-1-containing cation exchange material with at least about 2 volumes, per volume of said cation exchange material, of a 0.02M acetic acid solution, followed by either (1) about four volumes of a 0.02M sodium acetate solution having a pH of 5 and containing 0.2M sodium chloride or (2) at least four volumes of a 0.05M sodium acetate solution having a pH of 5 and then at least four volumes of a 0.05M sodium acetate solution having a pH of 5.5 or (3) about four volumes of a 0.05M sodium acetate solution, pH 5.5, then about four volumes of a solution containing 0.05M NaCl in 50 mM sodium acetate pH 5.5 and then about four volumes of a solution containing 0.1M NaCl in 50 mM sodium acetate, pH 5.5, (c) (1) eluting the adsorbed IGF-1 from said IGF-1-containing cation exchange matrix material of step (b) (1) by contacting said matrix material of step (b) (1) with a sufficient quantity of a solvent system comprising a 0.02M sodium acetate solution having a pH of 5.5 and containing 1.0M sodium chloride, or (2) eluting the adsorbed IGF-1 from said IGF-1-containing cation exchange matrix material of step (b) (2) by contacting said matrix material of step (b) (2) with about 8 volumes, per volume of said cation exchange matrix, of a linear gradient solution comprising 0 to 0.5M NaCl in 50 mM sodium acetate, pH 5.5 or (3) eluting the adsorbed IGF-1 from said IGF-1-containing cation exchange matrix material of step (b) (3) by contacting said matrix material of step (b) (3) with about 8 volumes of a solution containing 0.3M NaCl in 50 mM sodium acetate, pH 5.5, (d) contacting the eluate of step (c) (1) or those portions of the eluate of step (c) (2) or (c) (3) that contain, as the predominant form of IGF-1, intact, monomeric correctly folded IGF-1 with a sufficient volume of a buffered ammonium sulfate-containing solution, having a pH between about 4.0 and 7.0, so as to render the ammonium sulfate concentration of the eluate in the range of about 0.2 up to 2M, and the pH of the diluted eluate about 4.5, (e) contacting the product of step (d) with a sufficient quantity of a first hydrophobic interaction chromatography matrix under conditions suitable to adsorb in the range of about 95 up to 100% of said IGF-1 from said eluate, wherein said first hydrophobic interaction chromatography matrix is a butyl-substituted, poly(methacrylate)-supported hydrophobic interaction chromatography matrix; wherein at least about 0.05 liters, per gram of IGF-1 in said medium, of said hydrophobic interaction chromatography matrix are employed; and wherein said contacting is carried out at a temperature in the range of about 20° up to 25° C., (f) eluting the adsorbed IGF-1 from said first hydrophobic interaction chromatography matrix by contacting said matrix;
  (1) first with a quantity of a linear salt gradient of a buffered solution having a pH of about 4.5, or, preferably, an initial pH of about 5.0 and a final pH of about 4.0, sufficient to produce a substantially ammonium sulfate-free eluate, and,
  (2) preferably, with a buffered solution having a pH of about 4.0, then
  (3) with (i) a quantity of a linear gradient of a substantially ammonium sulfate-free buffered solution having an initial pH of about 4.0–4.5 sufficient to raise the pH of said eluate up to about 6.5–7.5, or (ii) a quantity of a buffered solution having a pH of about 6.5 to 7.5, wherein step (f) (3) (ii) is preferably carried out after step (f) (2)., (g) optionally, contacting at least a portion of the eluate fractions obtained in step (f) (3) (i) with a sufficient additional quantity of said first hydrophobic interaction chromatography matrix under conditions suitable to adsorb in the range of about 95 up to 100% of residual quantities of IGF-1 from said eluate, wherein said first hydrophobic interaction chromatography matrix is a butyl-substituted hydrophobic interaction chromatography matrix; wherein at least about 0.05 liters, per gram of IGF-1 in said medium, of said first hydrophobic interaction chromatography matrix are employed; and wherein said contacting is carried out at a temperature in the range of about 20° up to 25° C., (h) if optional step (g) was conducted, eluting the adsorbed IGF-1 from said first hydrophobic interaction chromatography matrix by contacting said matrix:
  (1) first with a quantity of a linear salt gradient of a buffered solution having a pH of about 4.5, or, preferably, an initial pH of about 5.0 and a final pH of about 4.0, sufficient to produce a substantially ammonium sulfate-free eluate, and,
  (2) preferably, with a buffered solution having a pH of about 4.0, then
  (3) with (i) a quantity of a linear gradient of a substantially ammonium sulfate-free buffered solution having an initial pH of about 4.0–4.5 sufficient to raise the pH of said eluate up to about 6.5–7.5, or (ii) a quantity of a buffered solution having a pH of about 6.5 to 7.5., (i) contacting those portions of the eluate from (f) (3) (i) or step (f) (3) (ii) or, optionally, the combined eluates from (f) (3) (i) and step (h) (3) (i) or (h) (3) (ii) which contain, as the predominant form of IGF-1, intact, monomeric, correctly-folded IGF-1, wherein said contacting is carried out with a sufficient quantity of a second cation exchange matrix material and under conditions suitable to adsorb in the range of about 95 up to 100% of said IGF-1 from said eluate, wherein said second cation exchange matrix is a sulfylmethylated or sulffyl-propylated matrix; wherein at least about 0.05 liters, per gram of IGF-1 in said medium, of said matrix are employed; and wherein said contacting is carried out preferably at a temperature in the range of about 20° up to 25° C., (j) contacting the IGF-1-containing cation exchange matrix material with at least one, up to about five volumes, per volume of said cation exchange matrix material, of a 0.05M sodium acetate solution, pH 4.5, and, preferably with 1–5 volumes of a 0.05M sodium acetate solution, pH 5.5, (k) eluting the adsorbed IGF-1 from said second cation exchange matrix material by contacting said matrix material with at least five volumes, relative to the volume of matrix, of a sodium chloride gradient, which is provided by combining, as a linear gradient, a first solvent system and a second solvent system;
wherein said first solvent system comprises a 0.05M sodium acetate solution, pH 5.5, and
wherein said second solvent system comprises a 0.05M sodium acetate/0.3M sodium chloride solution, pH 5.5, (1) after step (k), either (1) diluting the intact, monomeric, correctly-folded IGF-1-containing fractions of the eluate of step (k) with at least one volume of a buffered ammonium sulfate-containing solution, pH 4.0–7.0, so as to render the ammonium sulfate concentration of the eluate in the range of about 0.2 up to 2.0M and the pH of the diluted eluate about 4.5, and contacting the diluted eluate with a sufficient quantity of a second hydrophobic interaction chromatography matrix under conditions suitable to adsorb in the range of about 95 up to 100% of said IGF-1 from said eluate; wherein said second hydrophobic interaction chromatography matrix is a butyl-substituted, poly(methacrylate)-supported hydrophobic interaction chromatography matrix; wherein at least about 0.05 liters, per gram of IGF-1 in said medium, of said second hydrophobic interaction chromatography matrix are employed; and wherein said contacting is carried out at a temperature in the range of about 20° up to 25° C., or (2) concentrating the intact, monomeric, correctly-folded IGF-1-containing fractions of the eluate of step (k) and then contacting the concentrated material with a sufficient quantity of a size exclusion media having suitable pore size to effect resolution of the intact, monomeric correctly folded form of IGF-1 from substantially all multimeric forms of IGF-1 and (m) (1) after step (l) (1) eluting the adsorbed IGF-1 from said second hydrophobic interaction chromatography matrix by contacting said matrix:
  (i) first with a quantity of a linear salt gradient of a buffered solution having a pH of about 4.5, or preferably an initial pH of about 5.0 and a final pH of about 4.0, sufficient to produce a substantially ammonium sulfate-free eluate, and
  (ii) preferably with a buffered solution having a pH of about 4.0, then
  (iii) with either (1) a quantity of a linear gradient of a substantially ammonium sulfate-free buffered solution having an initial pH of about 4.0–4.5 sufficient to raise the pH of the eluate up to about 6.5–7.5 or (2) a quantity of a buffered solution having a pH of about 6.5 to about 7.5 or (m) (2) after step (l) (2), eluting said size exclusion matrix with 1–2 volumes of 0.05–0.1M ammonium acetate, pH 6, or 0.2M acetic acid so as to cause the intact monomeric correctly folded form of IGF-1 to be resolved from said multimeric forms of IGF-1.

The term "insulin-like growth factor-1" or "IGF-1 peptide" or simply "IGF-1", as used throughout the specification and in the claims, refers to the various forms of recombinantly produced IGF-1 (i.e., intact, monomeric, correctly-folded IGF-1, plus nicked, cleaved, multimeric and misfolded forms). As employed herein, the term "intact, monomeric, correctly-folded IGF-1" refers to forms of IGF-1 having substantially the same 70 amino acid sequence and tertiary structure as native IGF-1 (see Rotwein, et al., *J. Biol. Chem.* 261:4828–4832 (1986)), as well as biologically active analogs and derivatives thereof.

The first step in the invention purification process is to contact insulin-like growth factor-1-containing medium with a sufficient quantity of a first cation exchange matrix under conditions suitable to adsorb at least about 95% of the total IGF-1 from the medium.

Contacting of the insulin-like growth factor-1-containing medium with the first cation exchange matrix can be carried out in a variety of ways. For example, the first cation exchange matrix can be contained in a column through which the insulin-like growth factor-1-containing medium is percolated. Alternatively, the first cation exchange matrix can be contained in a closed vessel into which the insulin-like growth factor-1-containing medium is introduced, followed by stirring for a sufficient period of time to allow contacting of the matrix and fluid medium to occur, followed by decanting of the IGF-1-depleted medium from the IGF-1-containing first cation exchange matrix. As another alternative, the first cation exchange matrix can be added to the vessel containing the IGF-1-containing medium, followed by removal of IGF-1-depleted medium from the IGF-1-containing first cation exchange matrix.

Cation exchange matrix materials contemplated for use in the first contacting step of the present invention are well known in the art. Such exchange matrices include strong cation exchange matrices capable of having a high flow rate, i.e., having a high degree of strength so as to withstand high pressures, and, optionally, possessing a macroporous structure, and in addition, are capable of binding IGF-1 over a wide pH range. Exemplary strong cation exchange matrices include carboxymethylated and sulfonated cation exchange matrices. Matrix materials such as cellulose, polystyrene, dextrans, agarose, cross-linked agarose, and the like, can be used for the preparation of cation exchange matrices. Presently preferred cation exchange matrices for use in this first contacting step are sulfylpropylated matrices.

While not essential, it is frequently desirable to activate cation exchange matrices prior to contacting with IGF-1-containing medium. Such activation serves to condition the matrix for the IGF-1-containing medium which follows, and improves the efficiency of the matrix for adsorption of IGF-1 peptides and the separation of such peptides from other components in the medium. A typical activation procedure involves sequential contact of the cation exchange matrix with several column volumes of a dilute, weak acid (e.g., 2–5 volumes of 0.2M acetic acid), followed by several additional column volumes of a more dilute weak acid solution (e.g., 2–10 volumes of a 0.02M acetic acid solution).

The quantity of first cation exchange matrix material employed in the practice of the present invention can vary widely. Typically, at least about 0.03 l, up to 1 liter of matrix, per gram of IGF-1 contained in the medium, will be employed.

Contacting of IGF-1-containing medium with the first cation exchange matrix can be carried out under a variety of conditions. Typically such contacting is carried out for a time in the range of about 0.01 up to 1 hour, or longer, and at a temperature in the range of about 2° up to 30° C.; with temperature in the range of about 22° up to 25° C. being preferred.

Once IGF-1-containing broth has been maintained in contact with the first cation exchange matrix for a period of time sufficient for IGF-1 to adsorb to the matrix material, it is desirable to remove the IGF-1-depleted medium from contact with the IGF-1-rich first cation exchange matrix. This can be accomplished in a variety of ways such as, for example, filtration, decantation, centrifugation, and the like. This contacting and separation can readily be accomplished in one operational step by passing the medium containing IGF-1 through a column of the first cation exchange matrix, wherein the column is equipped with a retaining means (e.g., a screen, support plate with holes, or the like), so as to retain the first cation exchange matrix in the column, yet allow fluid medium to pass therethrough. In this way, the IGF-1-depleted broth is allowed to merely flow through the first cation exchange matrix. In carrying out column chromatography in accordance with the present invention, a column bed height greater than about 10 cm is desirable, with a bed height of approximately 20 cm being especially preferred.

Once substantially all of the IGF-1 has been adsorbed onto the first cation exchange matrix, and prior to elution of the IGF-1 therefrom, it is desirable to contact the IGF-1-containing matrix with in the range of about 1 up to 10 volumes, relative to the volume of the first cation exchange matrix, of a dilute, weak acid; and thereafter, the matrix is further contacted with additional volumes of dilute, weak acid at a higher ionic strength (or at a higher ionic strength and pH) than the initial wash. This optional wash procedure serves to remove impurities which are not as tightly bound to the first cation exchange matrix as is the IGF-1. Exemplary dilute, weak acid solutions include approximately 0.02 molar acetic acid solutions or phosphoric acid solutions. Presently preferred wash systems include 20 mM acetic acid followed by 20 mM sodium acetate, pH 5, containing 0.2M NaCl or 20 mM acetic acid followed by 50 mM sodium acetate, pH 5, followed by 50 mM sodium acetate, pH 5.5, or a four-wash system consisting of: 20 mM acetic acid followed by 50 mM sodium acetate, pH 5.5, followed by 0.05M NaCl in 50 mM sodium acetate, pH 5.5, followed by 0.1M NaCl in 50 mM sodium acetate, pH 5.5.

Once substantially all of the IGF-1 has been adsorbed onto the first cation exchange matrix and optionally rinsed as described above, IGF-1 is then eluted from the IGF-1-containing matrix by contacting the matrix with a sufficient quantity of a solvent system which has a sufficiently high pH or ionic strength so as to displace substantially all of the IGF-1 from the matrix. A solvent system which has a sufficiently high pH or ionic strength to accomplish the desired elution is a solvent system which has a higher ionic strength than the aqueous medium with which the matrix material is equilibrated, or, alternatively, has a pH of greater than the aqueous medium with which the matrix material is equilibrated. Elution is accomplished by increasing the pH or ionic strength of the solvent system. A solvent system which has a "sufficiently high pH or ionic strength" to accomplish the desired elution is one wherein the pH or ionic strength has been sufficiently altered so as to substantially increase the partitioning of IGF-1 peptides into the mobile phase from the stationary phase.

Solvent systems contemplated for use in this elution step include dilue buffered solutions of a weak acid, at a pH of about 5.5, and containing about a 0.2–1M concentration of an ionic salt, e.g., sodium chloride, and the like. Presently preferred solvent systems for use in this elution step are (1) a 0.02M sodium acetate solution having a pH of about 5.5, further containing about 1M sodium chloride, (2) a linear gradient solution comprising 0–0.5M NaCl in 50 mM sodium acetate, pH 5.5 or (3) a 0.05M sodium acetate solution containing 0.3M NaCl, pH 5.5. Where the elution step is carried out with a 0.05M sodium acetate solution, pH 5.5, containing 0.3M NaCl (i.e., solvent system (3) above), it is particularly preferred to use the four-wash system consisting of 20 mM acetic acid followed by 50 mM sodium acetate, pH 5.5, followed by 0.05M NaCl in 50 mM sodium acetate, pH 5.5, followed by 0.1M NaCl in 50 mM sodium acetate, pH 5.5 prior to the elution step.

The quantity of the eluting solvent system employed can vary widely. Typically, in the range of about 3–10 volumes of the solvent syste, per volume of first cation exchange matrix, will be employed.

Elution of IGF-1 from the IGF-1-containing cation exchange matrix can be carried out under a variety of conditions. Typically, a temperature in the range of about 2° up to 30° C. will be employed. Typically, elution time will be relatively short, falling in the range of about 0.01 up to 1.0 hour, although longer or shorter times can also be employed.

Partially purified IGF-1-containing medium which has been eluted from the first cation exchange matrix is then contacted with a sufficient quantity of a first hydrophobic interaction chromatography matrix under conditions suitable to adsorb in the range of 95% up to 100% of the IGF-1 from the IGF-1-containing medium. While such contacting can be carried out in both batch and continuous modes, it is presently preferred to contain the matrix material in a column, and to pass the IGF-1-containing medium therethrough. It is preferred to use a sufficient amount of matrix material to give a column bed height of about 20 cm.

Prior to contacting the eluate of the first cation exchange matrix with the first hydrophobic interaction chromatography matrix, the initial eluate is typically treated with a sufficient volume of a buffered salt-containing solution, pH 4.0–7.0, preferably 4.5–5.0, so as to render the salt concentration of the diluted eluate in the range of about 0.4 up to 1.0M, preferably 0.6M, and the pH of the diluted eluate about 4.5. By increasing the salt content of the medium, the binding affinity of IGF-1 for the hydrophobic interaction chromatography matrix is enhanced. Salts contemplated for such use are those salts which improve the hydrophobic interaction of IGF-1 and the hydrophobic interaction chromatography matrix, e.g., sodium sulfate, potassium sulfate, ammonium sulfate, potassium phosphate, sodium acetate, ammonium acetate, sodium chloride, sodium citrate, and the like. Broadly, the salt content employed will fall in the range of about 0.2 up to 2.0M; with a salt content of about 0.4 up to 1M being presently preferred. An especially preferred salt is ammonium sulfate, at a concentration of about 0.4–0.8M.

Hydrophobic interaction chromatography matrix materials contemplated for use in this next contacting of the present invention are alkyl- or aryl-substituted hydrophobic interaction chromatography matrices. Hydrophobic interactions are a phenomenon of great biological significance. They are one of the main forces that stabilize the three-dimensional structure of proteins. Hydrophobicity is the repulsion between a nonpolar compound and a polar environment such as water. Since the structure of water about a hydrophobic compound creates hydrophobic interactions, if one changes the structure of water by dissolving salts therein, the hydrophobic interactions are affected. Exemplary matrices include butyl-, octyl-, or phenyl-substituted hydrophobic interaction chromatography matrices. Supports contemplated for use as hydrophobic interaction chromatography matrices in the practice of the present invention include synthetic polymers, e.g., polystyrene, poly(methacrylates), etc.; cellulose, dextrans, agarose, cross-linked agarose, and the like. A presently preferred hydrophobic interaction chromatography matrix for use in the practice of the present invention is a butyl-substituted, poly(methacrylate) hydrophobic interaction chromatography matrix (e.g., TSK butyl Toyopearl-650M matrix).

Prior to use, hydrophobic interaction chromatography matrix can be activated, or after use, hydrophobic interaction chromatography matrix can be regenerated, employing the following sequential wash procedure:

in the range of 1–10 column volumes of water, in the range of 3–10 column volumes of a 0.5M sodium hydroxide solution, in the range of 1–10 column volumes of water in the range of 3–10 column volumes of a 50% aqueous methanol solution, and finally in the range of 1–10 column volumes of water, and thereafter, the column is equilibrated with in the range of 5–10 column volumes of a salt-containing acetate/phosphate buffer having a pH of 4.5, preferably about 5.0.

Quantities of first hydrophobic interaction chromatography matrix employed in the practice of the present invention can vary widely. Typically, in the range of about 0.05 up to 1 liter of matrix per gram of IGF-1 in the medium being treated will be employed.

Contacting of partially purified IGF-1-containing broth with the first hydrophobic interaction chromatography matrix can be carried out under a variety of conditions. Typically, such contacting is carried out for a time in the range of about 0.1 up to 30 minutes and a temperature in the range of about 15° up to 30° C.; with temperatures in the range of about 20° up to 25° C. being preferred.

Once substantially all of the IGF-1 has been adsorbed by the first hydrophobic interaction chromatography matrix, the IGF-1 is eluted from the first hydrophobic interaction chromatography matrix by contacting the matrix first under conditions suitable to remove some of the aberrant IGF-1 peptides from the matrix, without removing significant quantities of the intact, monomeric, correctly-folded form of adsorbed IGF-1 from the matrix; and therafter the matrix is contacted under conditions suitable to remove substantially all of the remaining adsorbed IGF-1 from the matrix. The IGF-1 content of eluate fractions can be determined by a variety of techniques, e.g., HPLC.

The initial elution of some of the aberrant IGF-1 peptides is accomplished by contacting the matrix with in the range of about 1 up to 10 volumes, relative to the volume of matrix, of a buffer system having a low conductivity, i.e., a buffer system of less than about 100 mM salt. Exemplary buffer systems include acetate buffers, phosphate buffers, lactate buffers, succinate buffers, Bis-Tris buffers, and the like, as well as mixtures thereto, having a pH of about 4.5. A quantity of such buffer is employed so as to produce a substantially salt-free eluate. Preferably, this initial elution of the first HIC matrix involves the use of a linear ammonium sulfate gradient starting at 20% saturated ammonium sulfate buffered at pH 5.0 with 50 mM sodium acetate/phosphate, and ending with 0% ammonium sulfate buffered at pH 4.0 with the same buffer. This is followed by a wash step using a pH 4.0 buffer without ammonium sulfate.

Elution of the remaining adsorbed IGF-1 from the matrix is accomplished by contacting the matrix with in the range of about 1 up to 10 volumes of a buffer system having an elevated pH, wherein said buffer is employed in a quantity sufficient to raise the pH of the eluate up to about 6.5–7.5.

Elution of IGF-1 from the IGF-1-containing hydrophobic interaction chromatography matrix can be carried out under a variety of conditions. Typically, a temperature in the range of about 15° up to 30° C. will be employed, with temperatures in the range of about 20° up to 25° C. preferred. Typically, elution time will vary as a function of column dimensions, matrix material, and the like. Flow of eluent through the column will typically fall in the range of about 10 up to 300 cm/h.

Optionally, a portion of the eluate of the first hydrophobic interaction chromatography matrix which is eluted employing buffer having an elevated pH may be applied to the same hydrophobic interaction chromatography matrix (after regeneration), and eluted a second time, employing the same two-stage or three-stage elution protocol described above. In this manner, additional quantities of the intact, monomeric, correctly-folded IGF-1 are obtained. Those eluate fractions which contain substantial quantities of intact, monomeric, correctly-folded IGF-1, plus substantial quantities of other forms of IGF-1 (e.g., 20% or greater content of multimeric form(s) of IGF-1) are likely candidates for such optional re-use of the first hydrophobic interaction chromatography matrix.

Next, the intact, monomeric, correctly-folded IGF-1-containing fractions of the eluates of the first hydrophobic interaction chromatography matrix may be then contacted with a sufficient quantity of a second cation exchange matrix under conditions suitable to adsorb in the range of about 95 up to 100% of the IGF-1 peptides from the eluate. This is conveniently accomplished by passing the medium containing the IGF-1 peptides through a column containing the second cation exchange material. This second cation exchange chromatography matrix is employed, where necessary, to remove "nicked" IGF-1 from IGF-1-containing fractions which contain "nicked" IGF-1, in addition to authentic IGF-1 and multimeric IGF-1. In particularly preferred embodiments of the present invention, protease-deficient strains of methylotrophic yeast may be used to produce recombinant IGF-1, wherein the levels of "nicked" IGF-1 may be practically negligible, in which case this second round of cation exchange chromatography may be optional, and, following hydrophobic interaction chromatography, the purification method may proceed to a gel filtration chromatography step, as described herein, if it is necessary to separate authentic IGF-1 from multimeric IGF-1.

Cation exchange matrices contemplated for use in this contacting step of the present invention are strong cation exchange matrices capable of high resolution, i.e., capable of resolving nicked IGF-1 from intact, monomeric IGF-1. Exemplary cation exchange matrices include carboxymethylated and sulfonated cation exchange media. A presently preferred cation exchange matrix for use in this contacting step of the present invention is a sulfonated agarose (e.g., Fast-Flow S-Sepharose or Toyopearl SP550C).

Quantities of the second cation exchange matrix employed in the practice of the present invention can vary widely. Typically, in the range of about 0.05 up to 1 liter of matrix per gram of IGF-1 in the medium being treated will be employed.

Contacting of the IGF-1-containing broth with the second cation exchange matrix can be carried out under a variety of conditions. Typically, such contacting is carried out for a time of at least about 0.1 minute and a temperature in the range of about 2° up 30° C.; with temperatures in the range of about 20° up to 25° C. being preferred.

Optionally, to reduce conductivity, if necessary, the medium applied to the second cation exchange matrix can be diluted with at least one volume of water (or a low conductivity buffer such as the column equilibration buffer) prior to contacting with the second cation exchange matrix. The pH of the diluted IGF-1-containing medium is preferably adjusted to about 4.5 prior to application to the second cation exchange matrix.

Prior to use, the second cation exchange matrix can be activated, or after use, the second cation exchange matrix can be regenerated, employing the following sequential wash procedure:

in the range of 1–10 column volumes of water, in the range of 3–10 column volumes of a 0.5M sodium hydroxide solution, in the range of 1–10 column volumes of water in the range of 3–10 column volumes of a 50% aqueous methanol solution, and finally in the range of 1–10 column volumes of water, and thereafter, the column is equilibrated with in the range of 3–5 column volumes of 0.5M sodium acetate, pH 4.5, and in the range of 10–20 column volumes of 0.05M sodium acetate, pH 4.5.

Once substantially all of the IGF-1 has been adsorbed onto the second cation exchange matrix, and prior to elution of the IGF-1 therefrom, it is desirable to contact the IGF-1-containing matrix with in the range of about 1 up to 5 volumes, relative to the volume of matrix, of a dilute buffer of a weak acid. Weak acids contemplated for this purpose include acetic acid and phosphoric acid. A presently preferred dilute buffer of a weak acid comprises a 0.05M sodium acetate solution having a pH of about 4.5. This optional wash serves to remove impurities which are not as tightly bound to the second cation exchange matrix as is the IGF-1. Preferably, this optional wash step involves use of a 0.05M sodium acetate solution having a pH of about 4.5 followed by a 0.05M sodium acetate solution having a pH of about 5.5.

Once substantially all of the IGF-1 has been adsorbed onto the second cation exchange matrix, and optionally washed as described above, IGF-1 is then eluted from the IGF-1-containing matrix by contacting the matrix with a sufficient quantity of a buffer system having a sufficient ionic strength so as to differentially displace substantially all of the IGF-1 peptides from the matrix. Typically at least one volume of eluent is employed for this purpose, with in the range of about 3 up to 12 volumes being preferred.

A convenient way to accomplish this differential displacement is to employ a sodium chloride gradient in a buffered solvent system. For example, a sodium acetate buffer having a pH of 5.5 can be employed with increasing amounts of sodium chloride added to the buffer over time. Thus, a linear gradient can be provided starting with a first solvent system comprising a 0.05M sodium acetate solution (pH 5.5) with increasing quantities of a second solvent system added thereto, wherein the second solvent system comprises a 0.05M sodium acetate/0.3M sodium chloride solution (pH 5.5).

Elution of IGF-1 from the IGF-1-containing cation exchange matrix can be carried out under a variety of conditions. Typically, a temperature in the range of about 2° up to 30° C. will be employed with temperatures in the range of about 20° up to 25° C. being preferred. Typically, elution times will vary as a function of column dimensions, matrix material, and the like. Flow of eluent through the column will typically fall in the range of about 10 up to 300 cm/h.

The eluate of the second cation exchange matrix can be treated either by a second hydrophobic interaction chromatography step, or, preferably, by a gel filtration process. Such treatment is employed to remove residual amounts of multimers from the substantially purified IGF-1-containing medium.

When gel filtration is employed to remove residual amounts of multimers from the substantially purified IGF-1-containing medium, the portion of the eluate from either the first hydrophobic interaction chromatography matrix or the second cation exchange chromatography matrix that contained, as the predominant form of IGF-1, intact, monomeric, correctly folded IGF-1, is contacted with a sufficient quantity of a gel filtration medium under conditions suitable to resolve substantially all of the monomeric IGF-1 from the multimeric forms. This is accomplished by passing the medium containing IGF-1 through a column containing the gel filtration medium. Gel filtration media contemplated for use in the practice of the present invention include size exclusion media having suitable pore size so as to allow differentiation between the desired intact, monomeric, correctly-folded form of IGF-1, and multimeric forms thereof. Exemplary gel filtration media include Sephadex, Sephacryl, Superdex, polymer-based resins, and the like.

Quantities of the gel filtration medium employed in the practice of the present invention typically are in the range of 1-10 l of gel filtration medium per gram of IGF-1 in the media being treated.

Contacting of the IGF-1-containing media with the gel filtration medium can be carried out under a variety of conditions. Typically, such contacting is carried out for a time of at least about 120 minutes and a temperature in the range of about 20°-25° C.

After use, the gel filtration medium can be regenerated employing the following sequential wash procedure:

In the range of 0.5-2.0 column volumes of water, in the range of 0.5-2.0 column volumes of 0.5M NaOH, in the range of 0.5-2.0 column volumes of 50% methanol, and finally, in the range of 0.5-2.0 column volumes of water; and thereafter, the column is equilibrated within the range of 1-5 column volumes of 0.05M ammonium acetate, pH 6, or 0.2M acetic acid.

Once the IGF-1-containing medium has been applied to the gel filtration medium, IGF-1 is then eluted from the gel filtration medium by contacting the gel filtration medium with a sufficient quantity of eluent so as to facilitate differential movement of multimeric and monomeric IGF-1 through the gel filtration medium without significant, irreversible adsorption of protein to the matrix. Typically, at least 1 volume of eluent is employed for this purpose, with in the range of about 1 up to 1.5 volumes being preferred. Exemplary eluents for use in eluting IGF-1 from the gel filtration medium include salt-containing buffers such as 50 mM ammonium acetate, pH 6.0, or low conductivity buffers such as 0.2M acetic acid. While essentially any gel filtration material having a suitable pore size may be chromatographed with a salt-containing buffer as described herein, it is especially preferred to conduct gel filtration chromatography using a gel filtration matrix which employs a polymer-based resin, most preferably Toyopearl HW50F (TosoHaas, Philadelphia, Pa.), and to elute with an acetic acid solution, such as 0.2M acetic acid.

Elution of IGF-1 from the IGF-1-containing gel filtration medium can be carried out using various conditions. Typically a temperature in the range of about 20°-25° C. will be employed. Typically, elution times will vary as a function of column dimensions, gel filtration medium and the like. Flow of eluent through the column will typically fall in the range of 5 up to 50 cm/hr.

When a second hydrophobic interaction chromatography matrix is employed instead of gel filtration, and prior to contacting the portion of the eluate of the second cation exchange matrix with a second hydrophobic interaction chromatography matrix, the eluate of the second cation exchange matrix which contains substantial quantities of intact, monomeric correctly-folded IGF-1 is optionally diluted with a sufficient volume of a buffered salt-containing solution having a pH of about 4.0 to about 7.0, preferably about pH 4.5-5.0 so as to render the salt concentration of the diluted eluate in the range of about 0.4 up to 1.0, preferably 0.6M.

The portion of the eluate of the second cation exchange matrix which contains substantial quantities of intact, monomeric correctly-folded IGF-1 is then contacted with a second hydrophobic interaction chromatography matrix, which can be the same as or different than the first hydrophobic interaction chromatography matrix previously used.

Quantities of the second hydrophobic interaction chromatography matrix and conditions of contacting for this step are similar to those employed in the previous contacting of the IGF-1-containing medium with the first hydrophobic interaction chromatography matrix.

Once substantially all forms of IGF-1 (i.e., those forms which are still present at this stage of the purification procedure) have been adsorbed by the second hydrophobic interaction chromatography matrix, the IGF-1 is eluted from the matrix by again contacting the matrix, as previously described for the first hydrophobic interaction chromatography matrix. Thus, the matrix is treated first, under conditions suitable to remove substantially all remaining forms of IGF-1 other than the intact, monomeric, correctly-folded form of IGF-1 from the matrix, without displacing significant quantities of the intact, monomeric, correctly-folded form of IGF-1; and thereafter, the matrix is treated under conditions suitable to remove substantially all of the remaining adsorbed IGF-1 from the matrix.

Elution of forms of IGF-1 other than the intact, monomeric, correctly-folded form of IGF-1 (predominantly multimeric forms of IGF-1) is accomplished employing a buffer system having a low conductivity. Such a buffer will promote the elution of primarily multimeric forms of IGF-1. An examplary buffer system useful for such purpose is a linear salt gradient of a buffered solution having a pH of about 4.5 in a quantity sufficient to produce a substantially salt-free eluate. Preferably, a linear ammonium sulfate gradient starting at 20% saturated ammonium sulfate buffered at pH 5.0 with 0.05M sodium acetate/phosphate and ending with 0% ammonium sulfate buffered at pH 4.0 with the same buffer is used for this purpose. This is followed with a wash step using a pH 4.0 buffer without ammonium sulfate.

Elution of the remaining adsorbed IGF-1 from the matrix is accomplished employing a buffer system having a pH higher than the pH of the aqueous medium used to equilibrate the HIC matrix. A convenient means to provide such a medium is a linear gradient of a substantially salt-free buffered solution having an initial pH of about 4.0, wherein the pH of this buffer solution is gradually raised to about 6.5–7.5. Alternatively, the medium may be a buffered solution having a pH of about 6.5 to about 7.5.

As previously described with reference to the first hydrophobic interaction chromatography matrix, a portion of the eluate of the second HIC matrix which is eluted employing elevated pH buffer, and containing predominantly multimeric forms of IGF-1, plus small amounts of intact, monomeric, correctly-folded IGF-1, can be reapplied to the second hydrophobic interaction chromatography matrix, then re-eluted employing the same two-stage elution protocol described above.

The substantially purified product obtained from the above-described multi-step process can optionally be treated to remove residual salts from the purified product, and to concentrate the medium containing the purified product. For example, salt removal can be accomplished by gel filtration, diafiltration, and the like, while concentration of the medium containing purified product can be accomplished by lyophilization, diafiltration, and the like.

The medium from which IGF-1 is recovered according to the invention method for IGF-1 purification can vary widely. The recovery of natural, synthetic and/or recombinant materials is presently contemplated. Preferably, medium containing at least about 0.01 grams of IGF-1 peptides per liter of medium will be employed for the practice of the present invention.

Synthetic sources of IGF-1 from which intact IGF-1 monomer can be recovered and purified in accordance with the present invention include recombinant modified yeast, bacteria and/or mammalian cells containing one or more DNA sequences operably encoding IGF-1 peptides. Presently preferred are yeast species selected from the genus Pichia, wherein the yeast are transformed with at least one DNA fragment capable of expressing IGF-1; especially where IGF-1 is expressed from a construct comprising, in the direction of transcription, the following DNA sequences:
(i) a promoter region of a methanol responsive gene of *P. pastoris*, e.g., the AOX1 promoter,
(ii) a DNA sequence encoding a polypeptide consisting of:
  (a) the *S. cerevisiae* alpha mating factor (AMF) prepro sequence, including a processing site selected from the group consisting of lys-arg; and lys-arg-(glu-ala)$_x$, wherein x is an integer between 1 and about 3, and
  (b) an insulin-like growth factor-1 (IGF-1) peptide; and
(iii) a transcription terminator functional in *P. pastoris*, wherein said DNA sequences are operationally associated with one another for transcription of the sequences encoding said polypeptide.

The specific *Pichia pastoris* strains G+IGF201S1, G+IGF201S2, G+IGF201S6, G+IGF201S10, G+IGF202S3, G+IGF202S5, G+IGF204S2, G+IGF204S8, G+IGF206S2, G+IGF206S5, G+IGF206S8, G+IGF206S9, G+IMB202S2, G+IMB204S14, G+IMB206S1, G+IMB206S3, G−IMB206S1, G−IMB206S2, or G−IMB206S3 are presently preferred because they have proven to produce high levels of IGF-1 upon fermentation. These specific presently most preferred strains are prepared and caused to express IGF-1 as described in copending application Ser. No. 578,728, to which application the reader is directed for additional detail as to the preparation of the strains and expression of IGF-1 therefrom. Strains of *P. pastoris* which are deficient in proteolytic activity and which produce high levels of IGF-1 and reduced levels of nicked IGF-1 upon fermentation are described in co-owned U.S. application Ser. No. 678,916, filed Apr. 1, 1991 and co-owned PCT International Application No. US91/06452, filed Sep. 4, 1991, the disclosures of which applications are incorporated herein. An especially preferred *P. pastoris* strain, which produces high levels of authentic IGF-1 and reduced levels of nicked IGF-1, is M+IMB206S1.

When the IGF-1 to be purified is contained in the fermentation broth from a fermentation operation, it is preferred to separate cellular and particulate material from the fermentation broth prior to the intial contacting of the IGF-1-containing medium with the first cation exchange matrix. Preferably, the IGF-1 to be purified is contained in a substantially cell-free fermentation broth from a high cell density fermentation operation. In this situation, the broth is optionally diluted with a buffered medium prior to contacting the broth with the first cation exchange matrix. The buffer employed for this purpose should have a low conductivity, and should be of about the same pH as the media used to equilibrate the first cation exchange matrix.

The invention will now be described in greater detail with reference to the following non-limiting examples.

Examples

EXAMPLE 1: CHARACTERIZATION OF RECOMBINANT PROTEINS IN THE BROTH OF IGF-1-SECRETING STRAINS OF *PICHIA PASTORIS*

Recombinant IGF-1 was produced by growing IGF-1-secreting strains of *P. pastoris*, G+IMB204S14 and M+IMB206S1 (described in U.S. patent application Ser. No. 578,728, filed Sep. 4, 1990, and U.S. Ser. No. 678,916, filed Apr. 1, 1991, and International Application No. PCT/US91/06452, filed Sep. 4, 1991), in a 10-liter fermentation conducted according to the following three-stage high cell density batch fermentation procedure:
1) growth on excess glycerol,
2) growth on limited glycerol, and
3) growth on limited methanol.

Cells are initially grown on glycerol in a batch mode. Because glycerol strongly represses the AOX1 promoter, the IGF-1 gene, which is regulated by this promoter, is not expressed during this phase. Following exhaustion of the glycerol, a limited glycerol feed is initiated. Glycerol does not accumulate during this phase, but cell mass increases, and the AOX1 promoter is de-repressed. Finally, in the third phase, a methanol feed is initiated which fully induces the AOX1 promoter for the production of IGF-1.

Correctly folded, intact monomeric IGF-1 was purified from the broth of 10-liter fermentations using the invention combination of cation exchange chromatography, hydrophobic interaction chromatography (HIC) and gel filtration chromatography.

A. Ten-Liter Fermentations of *P. pastoris* Strain G+IMB204S14 and M+IMB206S1

A 15-liter fermentor (Biolafitte; Princeton, N.J.) containing 3.5 liters of 10× basal salts (42 ml 85% phosphoric acid)/l, 1.8 g calcium sulfate.$2H_2O$/l, 28.6 g potassium sulfate/l, 23.4 g magnesium sulfate.$7H_2O$/l, 6.5 g potassium hydroxide/l) and 220 g glycerol in a total volume of 5.5 liters was sterilized. After the fermentor cooled, 24 ml $PTM_1$ trace salts (6.0 g cupric sulfate.$5H_2O$/l, 0.08 g sodium iodide/l, 3.0 g manganese sulfate.$H_2O$/l, 0.2 g sodium molybdate.$2H_2O$/l, 0.02 g boric acid/l, 0.5 g cobalt chloride/l, 20.0 g zinc chloride/l, 65.0 g ferrous sulfate.$7H_2O$/l, 0.20 g biotin/l, 5.0 ml sulfuric acid/l) were added and the pH was adjusted to 5.0 with the addition of 28% (concentrated) ammonium hydroxide. The pH was controlled with the addition of the same solution. Foaming was controlled with the addition of a 5% solution of Struktol J673. Temperature was maintained at 30° C., and dissolved oxygen was maintained above 20% of saturation by increasing agitation, aeration, reactor pressure or by supplementation of the air feed with oxygen. Inocula were prepared from cells of *P. pastoris* strain G+IMB204S14 or M+IMB206S1 grown overnight in buffered yeast nitrogen base (YNB) (11.5 g/L $KH_2PO_4$, 2.66 g/L $K_2HPO_4$, 6.7 g/L yeast nitrogen base, pH 6) containing 2% glycerol. The fermentor was inoculated with 500-700 mls of the cultured cells which had grown to an $OD_{600}$ of 2-8, and the batch growth regime was continued for 18-24 hours. At the point of glycerol exhaustion, indicated by an increase in dissolved oxygen concentration, a glycerol feed (50% w/v glycerol plus 12 ml/L $PTM_1$) was initiated at 100 ml/hour. At this point in the fermentation of strain G+IMB204S14 the set point of the pH controller was adjusted to 2.7-2.8. After 4 hours, the pH decreased to the set point value as a result of cellular metabolism. The glycerol feed was then terminated and a methanol feed (100% methanol plus 12 ml/L $PTM_1$) was initiated at 20 ml/hour. At this point in the fermentation of strain M+IMB206S1, the set point of the pH controller was adjusted to 2.8-3.0. After 4 hours of methanol feeding, the methanol feed rate was increased to 60 ml/hour and maintained at this rate for a total of approximately 72 hours, at which point the vessel was harvested.

B. Characterization of Recombinant Proteins in Fermentation Broth

Pichia-produced IGF-1 exists as several forms, including intact, monomeric, correctly-folded IGF-1, in the broth of fermentations of IGF-1-expressing *P. pastoris* strains, as evidenced by immunoblot and HPLC analyses of cell-free broth. Since the HPLC analysis (employing the protocol described in Example 3A1) of crude cell-free broth from the fermentation of *P. pastoris* strain G+IMB204S14 and M+IMB206S1 does not adequately resolve the various IGF-1 species, in order to distinguish the IGF-1 species by HPLC, the native *P. pastoris* proteins were removed through pretreating the broth by small-scale cation exchange chromatography.

1. Pretreatment of crude fermentation broth

Direct injection of crude *P. pastoris* broth onto HPLC usually did not result in a chromatogram with distinct peaks. In order to directly analyze the components of crude broth by HPLC (employing the protocol described in Example 3), a clean-up procedure was developed for removing endogenous *P. pastoris* contaminants using a small-scale cation exchange chromatography step. Several cation exchange systems were tested for this purpose: sulfylpropyl cation exchange capsules (FMC Pinebrook, N.J.) and Cuno (Meriden, Conn.)) and the use of a bulk cation exchanger (e.g., Sepharose Fast Flow (Pharmacia, Uppsala, Sweden), SP-Spherodex (IBF, Columbia, Md.), or Toyopearl SP650M and SP550C (TosoHaas, Philedelphia, Pa.)) in a 2-ml disposable polypropylene column (0.8×2.4 cm, BioRad, Richmond, Calif.) with an integrated 10-ml reservoir. Any of these systems yielded satisfactory results. The two systems routinely used to pretreat crude broth for quantitative HPLC analysis of the IGF-1 levels employed the Cuno cation exchange capsule or the SP-Spherodex or SP550C cation exchangers in a column format. The crude broth was cleaned up by cation exchange chromatography and injected directly onto an HPLC column. The resulting chromatogram clearly resolved the different IGF-1 species in broth.

a. Pretreatment using cation exchange capsules: The Cuno capsule is a 25-mm disk. The disk was first washed with 4 ml of 0.2M acetic acid, then equilibrated with 4 ml of 0.02M acetic acid. A volume of crude cell-free broth (1-10 ml) was diluted 1:2 with 0.02M acetic acid and loaded onto the disk. After loading, the disk was washed with 1.5 ml of 0.02M acetic acid and the IGF-1 was eluted with 4 ml 0.02M sodium acetate, pH 5.5, plus 1M NaCl. The first 1.5 ml of eluate contained 75-80% of the total IGF-1 and was usually the only elution volume collected. The capsule could then be regenerated by washing with 4 ml of 100% methanol.

b. Pretreatment using bulk cation exchanger in a column format: To the disposable column, 0.25 ml of prehydrated cation exchanger was added. The absorbent was first washed with 2 ml of 0.2M acetic acid, then equilibrated with 2 ml of 0.02M acetic acid. A volume of broth (1 ml) was loaded onto the column which was then washed with 1 ml of 0.02M acetic acid. All buffers and broth were carefully added to the column in an effort to avoid disruption of the column bed. Although some suspension of the absorbent usually occurred during addition of liquid to the column, it was not detrimental to sample binding or eluting. Broth samples and buffer were allowed to flow through the column by gravity. The IGF-1 was eluted with 2 ml of a 0.05M sodium acetate, pH 5.5, buffer containing 1M NaCl. The first milliliter of eluate contained 80-90% of the total IGF-1, eluted by the 2 ml of elution buffer. Periodically (approximately every 5-10 samples), the column was regenerated after the salt elution with a 50% methanol wash. Less often, the column was also regenerated with 0.5M NaOH. These columns retain their selective binding properties through many successive uses.

2. Characterization

The eluate obtained after small-scale cation exchange chromatography of cell-free broth from a fermentation of strain G+IMB204S14 or M+IMB206S1 contains all of the IGF-1 species (i.e., nicked, misfolded, multimeric and intact, correctly-folded monomer), which can be resolved by the HPLC protocol described in Example 3. The different peaks detected in the chromatogram from HPLC analysis of broth that had been subjected to cation exchange chromatography correspond to different forms of IGF-1 produced in recombinant *P. pastoris* fermentations. The identity of the proteins corresponding to these peaks was established by HPLC, immunoblot and SDS-PAGE analyses of broth and broth components (isolated by HPLC, gel filtration, cation exchange and hydrophobic interaction chromatography).

A chromatogram from HPLC analysis (conducted as described in Example 3A1) of broth from a fermentation of an IGF-producing *P. pastoris* strain contains a peak corresponding to protein that eluted from the HPLC column at approximately 10 minutes which respresents correctly folded, intact IGF-1 monomer. The identity of this protein was confirmed initially on the basis of its elution time by HPLC, which is identical to that of standard recombinant IGF-1 (Amgen, Thousand Oaks, Calif.). Furthermore, the protein with an HPLC elution time of approximately 10 minutes was purified, as described in Example 2 and subjected to additional analyses. SDS-PAGE analysis of reduced and non-reduced samples of the purified protein yielded identical results, revealing that it is a 7.7-kDa intact protein that co-migrated with IGF-1 standard. Immunoblot analysis of the purified protein demonstrated that it is reactive with an antibody generated against the last 14 amino acids of IGF-1. Gel filtration chromatography of the purified protein revealed that it elutes as expected for an IGF-1 monomer of the correct size. Finally, amino acid analysis confirmed that the amino acid ratios of the purified protein correspond to those of standard IGF-1. Protein sequence analysis showed that the complete amino acid sequence of the purified protein is identical to that of authentic IGF-1.

The protein that elutes from an HPLC column at approximately 8.6 minutes was tentatively identified as misfolded IGF-1. This protein was isolated by HPLC and hydrophobic interaction chromatography, and characterized by SDS-PAGE, immunoblot and protein sequence analysis (see Examples 3C and 3F for protocols). SDS-PAGE analysis of reduced and non-reduced samples of this protein showed that this form migrated with authentic monomeric IGF-1 and that it was not a nicked form of IGF-1 (i.e., that it was an intact protein in which the primary structure was held together solely by peptide bonds, as opposed to a cleaved IGF-1 molecule consisting of two or more peptide fragments held together by disulfide bonds). Western blot analysis of this protein using an antibody directed against the C-terminus of IGF-1 showed that it was immunoreactive. Amino-terminal protein sequencing of this protein also confirmed that the molecule was intact since only one amino-terminal sequence, that of authentic IGF-1, could be identified. Furthermore, reduced samples of this putative misfolded form of IGF-1 which had been treated with dithiothreitol, co-elute with reduced samples of authentic IGF-1 when subjected to reverse phase HPLC. These results suggest that this form is a misfolded species of IGF-1.

The proteins that elute from an HPLC column at approximately 10.5-11.5 minutes were identified as nicked or degraded forms of IGF-1 (i.e., IGF-1 molecules containing two or more peptide fragments, generated by cleavage of one or more peptide bonds, and held together by disulfide bonds). There appears to be at least two peaks by HPLC chromatographic analysis of cleaned up broth that correspond to nicked forms of IGF-1. The protein represented by the major peak (eluting at 10.7 minutes) was isolated during the S-Sepharose cation exchange step of the IGF-1 purification process (see Example 2C).

In silver-stained SDS-PAGE gels of non-reduced samples of this isolated IGF-1 species, the molecule comigrated with IGF-1 standard and appeared as a single band. However, in silver-stained gels of reduced samples of the isolated material, a doublet was detected representing two peptides of approximately 3-4 kDa each (approximately half the size of intact IGF-1). The position of this doublet in the gel correspond to that of the lower of the two bands detected below the band representing intact IGF-1 in gels containing reduced samples of crude cell-free broth. These results indicate that this molecule is cleaved or nicked and held together by disulfide bonds. Amino-terminal protein sequence analysis of the protein confirmed that the molecule was nicked prior to residue 40 since two amino-termini were detected: one beginning with residue 1 of IGF-1 and one beginning with residue 40 of IGF-1. Immunoblot analysis of reduced and non-reduced samples of this isolated nicked IGF-1 molecule revealed that it is less reactive than intact IGF-1 with the antibody directed against the C-terminus of IGF-1.

Two additional nicked species were identified in protein sequence analysis of IGF-1 recovered from the first cation exchange chromatography step of the purification process (see Example 2A). Either or both of these species could correspond to the minor peak in the HPLC chromatogram of cleaned-up cell-free broth (protein eluting at 11 minutes). The amino-terminus of the C-terminal fragment of one of these nicked molecules begins at residue 25 of IGF-1. The amino terminus of the C-terminal fragment of the other nicked species detected in the broth of strain G+IMB204S14 begins at residue 14 of IGF-1.

The last set of proteins detected by HPLC of cell-free broth, which elute from the HPLC column after 11.5-16 minutes, appear to be disulfide-bonded multimer forms of IGF-1. The presence of disulfide-bonded IGF-1 multimers in *P. pastoris* broth was indicated in SDS-PAGE gels of broth and immunoblots of the gels. The putative multimers migrated as IGF-1 dimers and trimers on non-reduced SDS-PAGE gels and were reactive with antibody directed against the C-terminus of IGF-1 in immunoblots. When these multimers were reduced, they co-migrated with standard monomer IGF-1 in SDS-PAGE gels and co-eluted with monomer IGF-1 in HPLC, which indicates that they contain disulfide-bonded IGF-1 monomers. Furthermore, multimer IGF-1 (apparent dimer and trimer) species were isolated on a gel filtration column and analyzed by HPLC (see Example 3B). The isolated multimer eluted from the column at 12-14 minutes, which corresponds to the elution times of the proteins in broth that were proposed to be multimers of IGF-1.

EXAMPLE 2: PURIFICATION OF CORRECTLY FOLDED, INTACT IGF-1 MONOMER FROM P. PASTORIS FERMENTATION BROTH

The process for the purification of correctly folded, intact monomeric IGF-1 from *P. pastoris* fermentation broth was based on a combination of cation exchange, hydrophobic interaction and gel filtration chromatography. This process was applied to the purification of correctly-folded, intact, monomeric IGF-1 from the broth of 10-liter fermentations of strain G+IMB204S14 and M+IMB206S1.The material obtained after each step in the purification of IGF-1 was qualitatively and quantitatively (by HPLC; see Example 3A for a description of the protocol) analyzed to determine the IGF-1 yield and purity of the product. The results of these analyses are tabulated in Tables I and II.

TABLE I

RESULTS OF PURIFICATION OF IGF-1 FROM CELL-FREE FERMENTATION BROTH OF *P. PASTORIS* STRAIN G+IMB204S14

| Purification Step | Intact IGF-1 Monomer by HPLC | | | Volume liters |
|---|---|---|---|---|
| | mg | Percent purity | Percent Recovery | |
| Cell-Free Broth | 525 | ND | 100 | 6.0 |
| Recovery from SP-250 Capsule | 425 | 34 | 81 | 0.84 |
| Butyl HIC | 235 | 74 | 45 | 0.59 |
| S-Sepharose | 203 | 91 | 39 | 0.20 |
| Final HIC | 147 | >97% | 28 | 0.32 |

ND = not determined

TABLE II

Purification of IGF-1 from Cell-Free Broth of *P. pastoris* Strain M+IMB206S1

| STEP | PROTEIN grams (BCA) | TOTAL IGF-1 grams (HPLC) | AUTHENTIC IGF-1 grams (HPLC) | OVERALL YIELD (%) |
|---|---|---|---|---|
| CELL-FREE BROTH | 81.0 | 2.443 | 0.976 | 100 |
| SP-RECOVERY | 5.0 | 1.607 | 0.729 | 75 |
| BUTYL HIC | 1.006 | 0.673 | 0.613 | 63 |
| S-SEPHAROSE | 0.860 | 0.580 | 0.531 | 54 |
| GEL FILTRATION | 0.620 | 0.490 | 0.490 | 49 |
| CONCENTRATION/ DIAFILTRATION | 0.420[a] | 0.463 | 0.453 | 46 |

[a]The final sample was analyzed by amino acid analysis.

A. Recovery of IGF-1 from Fermentation Broth

Pichia-produced IGF-1 was recovered from crude fermentation broth using either a CUNO radial flow Zeta Prep SP-250 (sulfylpropyl) cation exchange capsule or a 5-cm column packed with Toyopearl SP550C ion exchanger (TosoHaas, Philadelphia, Pa.).

1. Preparation of cell-free broth

Approximately 10 liters of a fermentor culture of *P. pastoris* strain G+IMB204S14 or M+IMB206S1 was centrifuged at 6500×g for 20 minutes to separate broth from the cells. Approximately 5 to 6 liters of cell-free supernatant from broth of G+IMB204S14 was obtained containing 400–600 mg of intact IGF-1 monomer, as measured by HPLC (see Example 3A). An additional 40–60 mg of intact IGF-1 monomer was recovered from the cell pellet by washing the pellet with approximately 4–5 liters of 20 mM acetic acid and again removing the cells by centrifugation. The supernatant from the first centrifugation was diluted 1:1 with 20 mM acetic acid and combined with the cell pellet wash. Approximately 7.3 l of cell-free broth was recovered from crude broth of M+IMB206S1 and contained approximately 976 mg of authentic IGF-1. The complete cell-free broth preparations were then filtered through a Whatman GF (glass fiber) filter.

2. Preparation of cation exchanger a. Cation exchange capsule: A radial flow ZetaPrep SP-250 (sulfylpropyl) cation exchange capsule (CUNO, Meriden, Conn.) was equilibrated by pumping through the capsule three column volumes (750 ml) of 0.2M acetic acid, followed by four column volumes of 20 mM acetic acid at a flow rate of 50 ml/minute. All steps in this first cation exchange contacting were conducted at approximately 4° C.

b. Toyopearl SP550C cation exchange chromatography column: Alternatively, a 5-cm diameter column was packed with 250 ml Toyopearl SP550C ion exchanger in 0.5M NaCl at a rate of 100 ml/minute (300 cm/hr). After packing, a bed height of 12 cm was measured for a bed volume of 235 ml. The column was regenerated with six separate washes: 1 l of 1M NaCl followed by 250 ml of water, both at a flow rate of 50–75 ml/min, 1 liter of 0.5M NaOH at 10–20 ml/min, 250 ml water at 25–50 ml/min, 1 l of 50% methanol at 10–20 ml/min, 250 ml water at 25–50 ml/minute. For storage, the column was placed in 20% ethanol at room temperature. To prepare the column for loading, 500 ml of 200 mM acetic acid was applied to the column at 50–75 ml/min followed by equilibration with 1.5–2.0 l of 20 mM acetic acid at 50–75 ml/min. All operations on this column were carried out at room temperature.

3. Sample application and wash a. Cation exchange capsule: The diluted, filtered cell-free broth from a fermentation of G+IMB204S14 (approximately 17 liters) was pumped onto the ZetaPrep capsule at a flow-rate of 50 ml/minute. Analysis of the flow-through obtained during loading of the cell-free broth onto the cation exchange capsule revealed that most of the colored material and native *P. pastoris* proteins in the broth passed through the capsule, as determined by SDS-PAGE and visual observation, whereas most of the total IGF-1 (>95%) in the broth was retained by the capsule, as determined by HPLC analysis of the flow-through.

After the diluted broth was loaded onto the capsule, the capsule was washed at a flow rate of 50 ml/minute with two column volumes of a buffered solution comprising 20 mM acetic acid followed by four column volumes of 20 mM sodium acetate, pH 5 (20 mM acetate plus 10M NaOH), containing 0.2M NaCl.

b. Toyopearl SP550C cation exchange chromatography column: The cell-free broth from fermentation of M+IMB206S1 was applied to the SP550C column at a flow rate of 50–75 ml/minute. The column was then washed with 1 l of 20 mM acetic acid at 50 ml/min followed by two 1-l washes with 50 mM sodium acetate, pH 5.0, and 50 mM sodium acetate, pH 5.5, respectively. Alternatively, the column was washed with four separated 1-l washes all at a flow rate of 50 ml/min: 20 mM acetic acid, 50 mM sodium acetate, pH 5.5, 0.05M NaCl in 50 mM sodium acetate, pH 5.5, 0.1M NaCl in 50 mM sodium acetate, pH 5.5.

4. Elution of IGF-1 a. Cation exchange capsule: The total IGF-1 was eluted by washing the capsule with six column volumes of a buffer comprising 20 mM sodium acetate, pH 5.5, and 1M NaCl (at a flow rate of 50 ml/minute). Fractions equivalent to one column volume (250 ml) were collected during the washes employing 0.2 and 1.0M NaCl-containing buffers, and assayed by HPLC to identify the IGF-1-containing fractions.

b. Toyopearl SP550C cation exchange chromatography column: IGF-1 was eluted from the column with a 2-liter linear gradient solution consisting of 0 to 0.5M NaCl in 50 mM sodium acetate, pH 5.5. Eluate fractions (25-30 ml each) were collected during the wash and elution of the column. Alternatively, IGF-1 was eluted with a solution consisting of 0.3M NaCl in 50 mM sodium acetate, pH 5.5.

5. Characterization of recovery a. Cation exchange capsule: The first fractions eluting during the 0.2M NaCl wash of the SP-250 ZetaPrep capsule that had been loaded with cell-free broth contained very little intact monomer IGF-1 but a significant amount of nicked and multimer IGF-1. Intact monomer IGF-1 started to elute in the final fraction of the 0.2M NaCl wash and the first three to four fractions from the 1M NaCl wash. The eluate fractions from the 1M NaCl elution were pooled. The pool contained approximately 425 mg of partially purified intact monomeric IGF-1 in a volume of 840 ml. Therefore, in the initial cation exchange step of the IGF-1 purification process conducted to recover IGF-1 from crude broth, a significant amount of the undesired nicked and multimer IGF-1 forms was eliminated from the IGF-1 preparation. Approximately 81% of the intact monomer IGF-1 was recovered in this step.

b. Toyopearl SP550C cation exchange chromatography column: Immunoblot and HPLC analysis of the flow-through obtained while loading the broth onto the column revealed negligible amounts of authentic IGF-1 but significant amounts of native Pichia protein contaminants and multimeric IGF-1. Therefore, a large portion of contaminant Pichia proteins did not bind to the matrix and were removed from the broth by passing through the column into the flow-through. In contrast, the majority of the IGF-1 bound to the matrix.

Quantitative HPLC analysis of eluate fractions revealed that a significant amount of nicked IGF-1 was removed from the preparation during the pH 5.5 wash (fractions 41-80) and the first portion of the salt gradient elution (fractions 81-119). As shown by HPLC analysis of a pool containing fractions 101-119 collected during the middle of the salt gradient elution, authentic IGF-1 began to elute from the column in these fractions which also contained misfolded and multimeric IGF-1.

The following criteria were used in the selection of the fractions that were pooled for further purification: (1) a level of less than 10% nicked IGF-1 in the fraction, and (2) a concentration greater than 100 mg/l for the authentic IGF-1 in the fraction. Based on these criteria and HPLC analyses of the remaining eluate fractions, fractions 120-155 were pooled, and the pool was prepared for further purification in the next step of the process. HPLC analysis of this pool revealed that authentic IGF-1 was the predominant IGF-1 species contained in the pool. Approximately 730 mg of the initial 976 mg of authentic IGF-1 contained in the broth was recovered in a volume of 1 liter for a yield of 75% for this step. This pool contained 21% misfolded IGF-1 (347 mg), 30% multimeric IGF-1 (488 mg), as well as 45% authentic IGF-1 (730 mg). Al thoughnot resolved in the chromatogram of this pool, nicked IGF-1 was also present in the pool at a level of approximately 40-50 mg (2-3%). At least 300 mg of nicked IGF-1 were removed from the preparation at this step as well as 400 mg of multimeric IGF-1.

A comparison of the total protein levels of the recovered pool (fractions 120-155), as determined by BCA (Pierce, Rockford, Ill.) assays, and the starting broth revealed that 94% of the total protein that was present in the cell-free broth had been removed from the preparation during the initial recovery step.

B. First Hydrophobic Interaction Chromatography Step

Following recovery of IGF-1 from cell-free *P. pastoris* broth using cation exchange chromatography, the IGF-1 was further purified by hydrophobic interaction chromatography (HIC) using TSK Butyl Toyopearl-650M matrix (TosoHaas, Philadelphia, Pa.). All steps in this first HIC contacting were conducted at 20°-25° C.

1. Column preparation

A variety of different conditions were investigated for the binding of IGF-1 to the HIC matrix, with particular attention paid to the concentration of ammonium sulfate in the medium and the pH of the medium. Typical of conditions used for HIC, IGF-1 was found to bind to the HIC matrix at high ammonium sulfate concentrations (i.e., greater than about 15% of saturation or about 0.6M $(NH_4)_2 SO_4$). Therefore, equilibration of the HIC matrix included the addition of ammonium sulfate.

A 2.5-cm diameter column was packed at 5-24 ml/min with approximately 37 ml or 123 ml of Toso-Haas Butyl Toyopearl-650M matrix in water. The column packed with 37 ml of matrix had a bed height of 7.5 cm, whereas the column packed with 123 ml of matrix had a bed height of 25 cm. The column was regenerated by washing with four or five separate washes at a flow rate of 800-1000 cm/hr: 200-250 ml of water, 200-800 ml of 0.5N NaOH, 100-800 ml of 50% methanol, and 100-250 ml of water. When the column was regenerated with five washes, a water (250 ml) wash was included between the NaOH and methanol washes. The matrix was then equilibrated with 200-750 ml of buffer (15-20% saturated ammonium sulfate, 50 mM sodium acetate, 50 mM sodium phosphate, pH 4.0-5.0). (One liter of 100% saturated ammonium sulfate is defined as containing 533 grams of the solid salt.) This ammonium sulfate concentration of the buffer is presently preferred for optimal binding of IGF-1 to the matrix. As is true for all buffered solutions described for use in the purification of IGF-1 by HIC, the HIC binding buffer was prepared from a 10× concentrated solution of 0.5M acetic acid and 0.5M monobasic sodium phosphate titered with sodium hydroxide to the appropriate pH value.

2. Sample preparation and application a. Sample of IGF-1 being purified from broth of G+IMB204S14: Approximately 425 mg of partially purified intact, monomeric, correctly-folded IGF-1 obtained from cell-free fermentation broth of strain G+IMB204S14 that had been passed through a Zeta-Prep cation exchange capsule was diluted to a total volume of three liters by addition of a buffer containing 5M sodium chloride, 0.5M sodium acetate, and 0.5M sodium phosphate, pH 4.0. One liter of an 80% saturated solution of ammonium sulfate was then slowly added to the three liters of diluted material. This resulted in a turbid solution containing precipitated IGF-1. Precipitate was removed by centrifuging the solution for 20 minutes at 10,000 rpm in a GSA rotor. The precipitate was dissolved in one liter of an acetate/phosphate buffer at pH 4.5. The four liters of soluble material (supernatant obtained after centrifugation) was adjusted to pH 4.5 and combined with the resuspended precipitate to yield a total of five liters. This 5-liter solution contained IGF-1 (425 mg), ammonium sulfate (16% of saturation), 40 mM sodium acetate, 40 mM sodium phosphate, pH 4.5 and 0.4M NaCl, and was loaded onto the HIC matrix. All solutions were applied to the column containing the HIC matrix at a flow rate of about 80-300 cm/hr, as per manufacturer's recommendations. To avoid precipitation of IGF-1 in subsequent steps of the purification process, the pH of the IGF-1-containing material was maintained at a pH of 4.5 or greater.

b. Sample of IGF-1 being purified from broth of M+IMB206S1: Eluate fractions from the initial SP550C cation exchange chromatography step that contained authentic IGF-1 at a specified level of purity (fractions 120-155) were pooled. This pool, which contained approximately 730 mg of partially purified authentic IGF-1 in a volume of 1 liter, was diluted to 2 liters by addition of 200 ml 10× stock of sodium acetate/phosphate pH 5.0 buffer and 800 ml of water containing 160 g ammonium sulfate to adjust the concentration of ammonium sulfate in the sample to 15% of saturation. The pH was adjusted to pH 5.0 with NaOH or HCl before slowly adding the ammonium sulfate solution. The IGF-1-containing solution was then loaded onto the column at 15 ml/minute (180 cm/hr).

3. Elution of IGF-1

During the course of this work aimed at the development of a method for the purification of IGF-1, we surprisingly discovered that the pH of the elution buffer employed in this HIC purification step altered the IGF-1 elution profile quite drastically. At pH 7.5, intact IGF-1 monomer starts to elute in a salt elution gradient at 0.6M ammonium sulfate, and is completely eluted when the ammonium sulfate concentration of the gradient is decreased to 0.2M. At lower pH values, intact IGF-1 did not begin to elute until the ammonium sulfate concentrations of the gradient had been decreased to lower values. If the pH of the buffer was less than 5, preferably 4.5, then the ammonium sulfate concentration could be reduced to 0% with very little intact IGF-1 monomer eluting from the column, although misfolded and multimeric IGF-1 are removed from the matrix under such conditions. Thus, decreasing the ammonium sulfate concentration of the column at low pH resulted in separation of misfolded and multimeric IGF-1 from authentic IGF-1. Then, the authentic IGF-1 was eluted from the matrix by increasing the pH.

Based on these findings, proteins are typically eluted from the HIC column in two or three steps. First, the ammonium sulfate concentration of the column is decreased from 20% of saturation to no ammonium sulfate using a 500-ml ammonium sulfate gradient solution buffered at pH 4.5-5.0 containing 50 mM sodium acetate, 50 mM sodium phosphate at a flow rate of 80-300 cm/hr. It is presently preferred that the ammonium sulfate gradient solution is a linear gradient starting at 20% saturated ammonium sulfate buffered at pH 5.0 with 50 mM acetate/phosphate and ending without ammonium sulfate buffered at pH 4.0 with the same buffer. This is followed by 400 ml of pH 4.0 buffer without ammonium sulfate. Because increasing the pH of the column surprisingly decreased the hydrophobic interactions in this system, in the next elution step, the pH was increased from about 4.0-4.5 to about 6.5-7.5 using a 0.5-2 liter buffer gradient (50 mM sodium acetate, 50 mM sodium phosphate) containing no ammonium sulfate.

4. Characterization of recovery a. Recovery from first HIC step in purifying IGF-1 from broth of strain G+IMB204S14: Eluate fractions (approximately 7.5 ml) were collected during each step of the elution process and analyzed by HPLC to identify IGF-1-containing fractions. The data were compiled and the elution profiles for each form of IGF-1 are shown graphically in FIG. 1. All of the misfolded IGF-1 eluted from the HIC matrix during elution of the column with the ammonium sulfate gradient solution (fractions 0-60). Approximately 75% of the multimer was removed from the matrix during the ammonium sulfate gradient elution (fractions 0-60) and during the first part of the pH gradient elution (fractions 60-84). However, the correctly-folded intact and nicked monomeric forms of IGF-1 remained bound to the matrix. During the second part of the elution step using a pH gradient solution (fractions 85-125), the intact monomer and nicked forms of IGF-1 eluted from the column.

The fractions separated into groups 1 and 2 in FIG. 1 were pooled into pools 1 and 2, respectively, for further purification. The first pool consisted of fractions collected during the period beginning when the ammonium sulfate concentration of the column was 0% (fraction 60) and extending to the time at which the majority of the multimer was removed from the matrix (fraction 84). The second pool consisted of fractions 85 to 125 collected during the pH gradient elution step. The chromatograms from HPLC analysis of these two pools indicate that very little multimer and practically no misfolded IGF-1 were present in the second pool, which consisted primarily of IGF-1 monomer and nicked IGF-1. Although not evident in HPLC analyses of diluted pool 2 samples, there was some residual multimer present in the second pool, as determined by SDS-PAGE and immunoblot analyses of these samples (see Example 3C).

b. Recovery from first HIC step in purifying IGF-1 from broth of strain M+IMB206S1: Fractions (25-30 ml) were collected during each step of the elution process and analyzed by HPLC (20-μl injections) and SDS-PAGE and immunoblot to identify IGF-1-containing fractions which could be pooled for further processing. Misfolded IGF-1 was removed in the ammonium sulfate gradient in fractions 1 through 18. The misfolded IGF-1 eluted from the column at approximately 90% purity.

The stained gel of a non-reduced sample of the pool of fractions 1-20 showed a broad band representing a high molecular weight protein, a band corresponding to a protein that comigrated with authentic IGF-1 monomer, and a faint band between the other two bands that could be a dimer form of IGF-1.

The pH 4 wash (containing no ammonium sulfate) removed the majority of multimeric IGF-1 that was bound to the resin. This 50 mM sodium acetate/phosphate pH 4 wash was applied to the column during the collection of fractions 19 through 30. After the individual fractions were characterized, fractions 21 through 29 were pooled and characterized by analytical HPLC. In the resulting chromatogram, the peak corresponding to multimer IGF-1 represented 75% of the peak area in the chromatogram. The chromatogram also revealed the presence of a small amount of authentic (48 mg) and nicked (13 mg) IGF-1 in this pool. The amount of authentic IGF-1 lost in this step is most likely a function of the capacity of the column.

When samples of the pH 4 wash pool (fractions 21-29) were examined by stained gel SDS-PAGE and western blot analyses, the predominance of multimer forms was evident. When not reduced, there were many high molecular weight forms in the sample that were not detected in reduced samples of the pool. Reduced samples of the pool consisted primarily of material that comigrated with monomer IGF-1.

The criteria used in the selection of authentic IGF-1-containing eluate fractions for further purification in the next step of the protocol were as follows: first, a level of less than 60% multimeric IGF-1 present in the fraction and second, a concentration of greater than 100 mg/L for the authentic IGF-1. Fractions 30-80, which were collected during the pH gradient elution, were selected and pooled to apply in the next step of the purification process. A total of 613 mg of the 730 mg of authentic IGF-1 loaded onto the HIC column was recovered in this pool. This yield corresponds to a recovery of 84% for this process step and a cumulative recovery of 63% from cell-free broth of strain M+IMB206S1. HPLC analysis of this pool also showed a level of 3 mg (0.5%) misfolded and 27 mg (4%) multimeric IGF-1. Although nicked IGF-1 was not resolved in the chromatogram, it was estimated that 21 mg (3%) of nicked IGF-1 was present in the pool. The purity of the authentic IGF-1 in this pool was therefore estimated at 92%. The overall level of protein in the recovered eluate pool from the HIC step was measured at 1 gram (Table II) or 20% of the total protein that was loaded onto the column.

Because all of the fractions collected during the pH gradient elution were pooled for further purification, the gradient elution can be replaced with a single 50 mM sodium acetate/phosphate, pH 7.5 step elution. A pH step elution decreases the volume of the recovered IGF-1 to approximately one liter and greatly simplifies the elution process. Therefore, the majority of the authentic IGF-1 is in the eluate collected during the pH step elution until the authentic IGF-1 concentration of the eluate is less than 100 mg/l. This pool can be combined with the final fractions of the pH 4 wash that contain authentic IGF-1.

5. Reapplication of sample to column and characterization of recovery

Only approximately 40% (170 mg) of the SP-250 capsule-purified intact, correctly-folded monomer IGF-1 from broth of strain G+IMB204S14 that was loaded onto the HIC column was recovered in the second pool of eluate fractions from the HIC column. FIG. 1 shows that a large amount of intact IGF-1 monomer (87 mg) was present in the first pool along with nicked and multimeric IGF-1. To recover additional intact monomer IGF-1, the first pool of eluate fractions was loaded back onto the HIC column and eluted according to the same procedure used in the initial HIC purification. An additional 65 mg of intact monomer IGF-1 was recovered from the HIC column. This pool 2 material was combined with the first pool 2 material to yield a final pool containing 235 mg of intact, correctly-folded monomer IGF-1 in a volume of 590 ml, at a purity of 74% (Table I). Therefore, approximately 55% of the SP-250 capsule-purified intact monomer IGF-1 that was loaded onto the butyl HIC column was recovered, reducing the total recovery to 45% at this stage in the purification process. This HIC step of the purification procedure thus effectively removed most of the multimeric and misfolded forms of IGF-1 from the preparation.

C. Cation Exchange Chromatography

The nicked and intact monomer IGF-1 species in the material obtained from HIC of Pichia-produced IGF-1 were separated by cation exchange chromatography using Fast Flow S-Sepharose (Pharmacia, Piscataway, N.J.) matrix. This matrix was prepared for chromatography by regeneration in a column using the same protocol as that described for regeneration of the HIC matrix (Example 2B). All steps in this second cation exchange chromatography procedure were conducted at 20°-25° C.

1. Preparation of column

A 2.5-cm diameter column was packed at 2-20 ml/min with approximately 35-80 ml of Pharmacia Fast Flow S-Sepharose in water. The column was equilibrated by passing 100-250 ml of 0.5M sodium acetate, pH 4.5, followed by 300-750 ml of 50 mM sodium acetate, pH 4.5, through the column. This low salt solution, buffered at a pH low enough to provide a net positive charge on the protein, was used to facilitate binding of IGF-1 to the negatively charged matrix.

2. Sample preparation and loading

The pool of IGF-1-containing eluate fractions obtained from HIC purification of partially purified IGF-1 from cell-free broth of strain G+IMB204S14 had a conductivity of 7 mmho and contained approximately 235 mg of intact IGF-1 monomer. The low-salt conditions used to elute the IGF-1 from the HIC column minimized manipulations of the eluate prior to ion exchange chromatography. The pH of the pool of IGF-1-containing eluate fractions from HIC purification of the IGF-1 sample from broth of strain G+IMB204S14 or strain M+IMB206S1 was adjusted to 4.5 and the volume of the pool was adjusted to one liter by addition of 50 mM sodium acetate, pH 4.5. The HIC-purified IGF-1 was loaded directly onto the cation exchange matrix, Fast Flow S-Sepharose, without further manipulation. After the protein was loaded on the column at 2-15 ml/min, the column was washed with approximately 100 ml of 50 mM sodium acetate, pH 4.5. The column was then additionally washed with 330 ml of 50 mM sodium acetate, pH 5.5, which additional wash is preferred.

3. Elution of IGF-1

The IGF-1 was eluted from the column using a 500- or 1000-ml 0 to 0.3M sodium chloride gradient buffered with 50 mM sodium acetate, pH 5.5. The higher pH reduced the ionic interaction between the proteins and the matrix, and the eluate fractions containing intact, correctly-folded, monomeric IGF-1, as determined by HPLC, were pooled. The matrix was stored in 20% ethanol.

Figure 2:
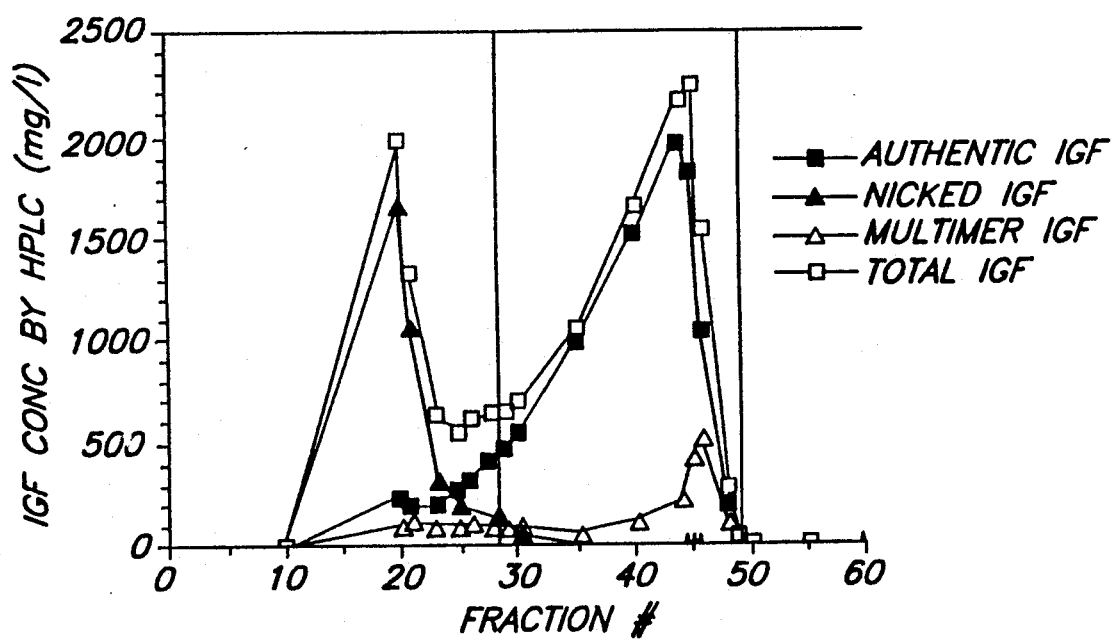
FIG. 2 is an elution profile for elution of various IGF-1 species from the second cation exchange matrix.

4. Characterization of recovery a. Recovery from second cation exchange chromatography in purifying IGF-1 from broth of strain G+IMB204S14: The elution profile for each of the IGF-1 species, which was generated from HPLC analysis of eluate fractions (approximately 8 ml each) collected during the gradient solution, is shown in FIG. 2. This cation exchange chromatography step completely resolved the nicked and intact monomer forms that were present in the preparation. Eluate fractions 28-50, obtained when the NaCl concentration of the gradient wash solution in the column ranged from 0.15 to 0.25M, were pooled. The results of SDS-PAGE, immunoblot, HPLC and gel filtration analysis (see Examples 3A, 3B, and 3C for protocols) of the pool of eluate fractions all show the presence of residual multimer (HPLC and gel filtration quantitation indicated a multimer level of 9%). Nevertheless, 86% (203 mg) of the intact, correctly-folded IGF-1 monomer that was loaded onto the Fast Flow S-Sepharose column was recovered in the eluate pool and the overall recovery at this stage of the purification process was 39% (Table I).

b. Recovery from second cation exchange step in purifying IGF-1 from broth of strain M+IMB206S1: Fractions (25-30 ml) were collected throughout the elution process and analyzed by HPLC to identify IGF-1-containing fractions which could be pooled for the next step in the purification process. In the pH 5.5 wash (fractions 6-17), approximately 10 mg of nicked IGF-1 were removed from the preparation. The presence of lower molecular weight peptides, which migrate more rapidly than IGF-1 standard, in an SDS-PAGE gel and corresponding immunoblot of a reduced sample of this pool that are not present in the non-reduced sample of the pool is indicative of the presence of nicked IGF-1. Nicked IGF-1 is the size of intact monomer in the non-reduced state but dissociates into two peptides upon reduction, each peptide being smaller than the intact molecule.

Fractions 21-29 were collected during the first portion of the salt gradient elution. As was the case in the early stages of the elution of the SP550C column with the linear salt gradient in the recovery step, there appeared to be some authentic IGF-1 eluting along with additional nicked IGF-1 in the first portion of the salt gradient elution of the S-Sepharose column. SDS-PAGE analysis of this pool showed forms of IGF-1 that migrated more slowly than IGF-1 standard under both non-reduced and reduced conditions. It is possible that these may be glycosylated or otherwise modified forms of IGF-1 which are present in very low levels.

The criteria used to select eluate fractions to pool for further purification were as follows: a level of less than 5% nicked IGF-1 present in the fraction and a concentration of greater than 150 mg/L for the authentic IGF-1. Fractions 30-45, collected during the second half of the salt gradient elution, were selected on the basis of these criteria and pooled to apply in the next step of the purification process. A total of 531 mg of authentic IGF-1 was recovered from the 613 mg of authentic IGF-1 that was loaded onto the column for a recovery yield of 87% for this process and a cumulative recovery of 54% from cell-free broth of strain M+IMB206S1. HPLC analysis of this pool showed that it also contained 3 mg (0.5%) misfolded, 3 mg nicked (0.5%), and 43 mg (7.5%) multimeric IGF-1.

The overall level of protein in the recovered pool from the S-Sepharose cation exchange chromatography step was measured at 0.86 grams (Table II). The pool was also analyzed by SDS-PAGE and immunoblot. The small amount of multimer IGF-1 contained in the pool was visible in the non-reduced SDS-PAGE stained gel.

D. Second Hydrophobic Interaction Chromatography Step or Gel Filtration Chromatography Step To reduce the multimer level in the otherwise pure intact monomer IGF-1 preparation, the pool of eluate fractions from the Fast Flow S-Sepharose cation exchange chromatography of IGF-1 partially purified from broth of strain G+IMB204S14 was loaded onto a regenerated TSK Butyl Toyopearl-650M matrix (see Example 2B for a description of matrix regeneration) for the second and final HIC step in the purification of IGF-1, as described in Example 2.D.1. below. All steps of this second HIC process were carried out at 20°-25° C.

It is presently preferred to remove residual multimer from the purified IGF-1 using gel filtration chromatography. As described in Example 3B also, multimeric and monomeric forms of IGF-1 are well resolved by gel filtration chromatography. The pool of eluate fractions from the Fast Flow S-Sepharose cation exchange chromatography of IGF-1 partially purified from broth of the strain M+IMB206S1 was loaded onto a gel filtration chromatography column as described in Example 2.D.2. below.

1. Second HIC step to remove multimer from pooled eluate from the second cation exchange step in the purification of IGF-1 from broth of strain G+IMB204S14 a. Sample preparation: Prior to loading the pool of eluate fractions onto the HIC column, the pool was diluted to 500 ml by adding 50 ml of a buffer solution containing 0.5M sodium acetate and 0.5M sodium phosphate, pH 4.5. To adjust the pH of the solution to 4.5, a sufficient quantity of 1N HCl was added. Water was then added to increase the total volume to 438 ml, and ammonium sulfate (63 ml of a solution which is 80% of saturation) was added slowly to yield 500 ml of a solution containing IGF-1 (203 mg), ammonium sulfate (10% of saturation), 50 mM sodium acetate, and 50 mM sodium phosphate, pH 4.5. No precipitate formed upon addition of ammonium sulfate to the eluate.

b. IGF-1 elution and reloading: The two-step elution procedure described in Example 2B was used to elute the IGF-1 from the HIC column. The eluate fractions were combined into two pools and, as described for the first HIC step (see Example 2B), pool 1 was loaded back onto the HIC column and eluted to recover intact IGF-1 monomer contained in the pool. The pool 2 eluates from the two elutions of the HIC matrix were combined to yield a single pool of purified IGF-1 monomer.

c. Characterization of recovery: HPLC analysis of the final eluate pool revealed that this preparation of intact IGF-1 monomer was greater than 97% pure and contained 147 mg of intact IGF-1 monomer in a volume of 320 ml for a final recovery of 28% of the intact IGF-1 monomer that was present in the cell-free broth (Table I).

2. Gel filtration chromatography of pooled eluate from the second cation exchange step in the purification of IGF-1 from broth of strain M+IMB206S1 a. Column preparation: A Superdex 75 16/60 prepacked 60 cm×1.6 cm diameter gel filtration column (Pharmacia, Uppsala, Sweden) was regenerated using 60 ml water at 1.4 ml/minute, 120 ml of 0.5M NaOH at a flow rate of 0.5 ml/minute, 60 ml of water at 0.5 ml/minute, 120 ml of 50% isopropyl alcohol at 0.5 ml/minute, and 60 ml of water at 0.5 ml/minute. The column was then equilibrated with at least two column volumes (250-350 ml) of 50 mM ammonium acetate after regeneration or storage. (The column was stored in 20% ethanol.) All operations using this column were carried out at room temperature.

Alternatively, a 2.5 cm diameter column was packed with Toyopearl HW50F size exclusion media (Toso-Haas, Philadelphia, Pa.) in 50 mM ammonium acetate, pH 6.0, at a flow rate of 6 ml/min (73 cm/hr) to a bed height of 92 cm (450 ml bed volume). The column was regenerated by washing the column with 150 ml water, 300 ml 0.5M NaOH, 150 ml water, 300 ml 50% methanol, followed by 150 ml water. The flow rate during regeneration was reduced to 2 ml/min due to high back pressure during the hydroxide wash. The column was stored in 20% ethanol and column operation was carried out at room temperature.

b. Sample preparation and application: As described in Example 2.C.4.b, fractions obtained during salt gradient elution of the S-Sepharose column that contained authentic IGF-1 at a specified level of purity were pooled. The pool (containing approximately 530 mg authentic IGF-1) was then concentrated from a volume of 420 ml to 60 ml in a 400 ml Amicon pressure cell using a YM2 membrane that retains proteins with a molecular weight greater than 2000 Da (i.e., a 2000 m.w. cut-off). The 60-ml concentrated pool was divided into 20 aliquots, each containing approximately 30 mg of authentic IGF-1. The aliquots were applied to the column individually, requiring a total of 20 chromatography runs for the batch. During sample application for each of the 20 cycles, the flow rate of the buffer (50 mM ammonium acetate, pH 6.0) was 0.7 ml/minute. Fifteen minutes after loading, the flow rate was adjusted to 1.4 ml/minute. After the monomer and multimer were eluted from the column, the next aliquot was loaded on the column, and the cycle was repeated. A larger column with a higher capacity would have reduced the number of cycles required.

Alternatively, when the Toyopearl HW50F column is used for gel filtration chromatography to remove residual multimer from partially purified IGF-1, 0.2M acetic acid can be used as the elution buffer. Interestingly, IGF-1 monomer eluted more slowly when the acetic acid buffer was used then when the 50 mM ammonium acetate buffer was used. It appears that there is some interaction involving this matrix and monomeric IGF-1 which retards the elution of monomeric IGF-1 and enhances the resolution of monomeric and multimeric IGF-1.

c. Elution of IGF-1: The column eluate was monitored with an on-line UV-absorbance detector set at a wavelength of 280 nm. When protein began to elute from the column, as indicated of the UV absorbance detector, fractions (7 ml each) of eluate were collected every 5 minutes until authentic IGF-1 monomer began to elute from the column, as indicated by a sharp increase in UV absorbance. At that point, 0.5-minute (0.7-ml) fractions were continually collected for approximately 3 minutes so that the transition fractions (i.e., fractions collected at the interface of multimer and monomer elution) could be analyzed. At the end of the 3-minute period, 5-minute fractions (7 ml each) were collected for the remainder of the monomer elution. Once the monomer had completely eluted, another aliquot containing 30 mg of IGF-1 was loaded onto the column and the elution process was repeated.

d. Characterization of recovery: The fractions that were collected from the gel filtration column for all 20 cycles were analyzed by HPLC. The IGF-1 material that was first to elute from the column was collected during the period beginning immediately after 64 ml of buffer had eluted from the column and ending immediately after 100 ml of eluate had eluted from the column (i.e., material in the 65th through 100th milliliter of eluate). HPLC analysis of this material that eluted from the gel filtration column as the first peak did not detect any protein (i.e., the HPLC chromatogram did not contain any peaks). Therefore, the concentration of this high molecular weight presumably multimeric IGF-1 species was estimated by comparing the absorbance of this material at 280 nm to that of the later eluting dimer IGF-1, which was quantifiable by HPLC analysis. SDS-PAGE analysis of this eluate pool showed a very high molecular weight protein located at the top of the gel under non-reducing conditions. Under reducing conditions, the band corresponding to this high molecular weight protein was of greatly diminished intensity and a band corresponding to monomer IGF-1 was present in the gel. In the western blots of these gels, a very faint band could be seen at the top of the blot containing the non-reduced sample, and the monomer band could be seen in the blot of the reduced sample.

The second peak on the gel filtration on-line detector chromatogram corresponded to material that eluted in the 100th through 120th milliliter of eluate. The majority of this material had an apparent molecular weight consistent with that of a trimer of IGF-1 as shown under non-reduced conditions on SDS-PAGE gels and corresponding western blots. In addition, this material contained a higher molecular weight species, as detected in these analyses. Under reducing conditions, the only band observed in the gel and immunoblot of this eluate pool corresponded to protein that co-migrated with standard IGF-1. The HPLC chromatogram for this pool revealed that IGF-1 trimer had a relatively long retention time (i.e., elution occurred from 14 to past 16 minutes).

The third peak on the gel filtration chromatogram corresponded to material that eluted in the 125th through 135th milliliter of eluate. HPLC analysis and SDS-PAGE and western analysis demonstrated that this eluate pool consisting primarily of IGF-1 dimer with small amounts of monomer and trimer IGF-1 as well. On an HPLC column, this pool eluted between 11 and 14 minutes.

Authentic IGF-1 started to elute in the 126th milliliter of eluate, which also contained a fairly high level of dimer IGF-1. However, the first 2.1 ml (1.5 minutes) of elution after the monomer began to elute contained only 0.2 mg of monomer. During the subsequent 2.1 ml of elution, 3 mg of monomer IGF-1 eluted, containing approximately 10% dimer IGF-1. This pool was recycled into the IGF-1 pool being loaded onto the column to improve the recovery yield of this process. If this pool was not recycled by reloading onto the column, then 10% of the total monomer IGF-1 would have been lost (3 mg of the 30 mg for each load). At that point, after a total of 130 ml of eluate had eluted, the multimer IGF-1 concentration had decreased to less than 3% and the remaining eluate was recovered until the end of monomer elution which occurred at the 150th milliliter of eluate. The monomer pools obtained after each of the 20 separate gel filtrations of the 20 aliquots of eluate from the S-Sepharose step were pooled to yield a total of 481 mg authentic IGF-1 in a volume of 600 ml. The yield for this step was 91% and the total yield for the purification process up to this point was 49% (Table II). HPLC analysis of the monomer pool indicated a purity of 98% and a multimer level of 0.9%. SDS-PAGE and western blot analysis of the monomer pool, in which only monomer IGF-1 was detected under both reducing and non-reducing conditions, was consistent with the results of HPLC analysis of the pool.

E. Diafiltration and concentration of purified IGF-1

1. IGF-1 purified from broth of strain G+IMB204S14

The final purified IGF-1 product obtained as pooled eluate (320 ml) from the second HIC step was concentrated to a volume of about 20 ml by filtration through a filter that retains proteins larger than 2000 Da (YM2 filter, Amicon, Darvers, Md.) in a 400-ml Amicon pressure cell. The buffer of the concentrated IGF-1 preparation was exchanged with 0.1M acetic acid by diluting the concentrated IGF-1 to 400 ml with 0.1M acetic acid and then concentrating the protein again by filtration to a total volume of approximately 20 ml. This process was repeated twice to accomplish a nearly complete buffer exchange. Diafiltration was conducted at a temperature of 2°–10° C.

2. IGF-1 purified from broth of strain M+IMB206S1

All of the eluate fractions from the gel filtration chromatography step containing monomer IGF-1 were pooled to yield a total volume of 600 ml containing 481 mg authentic IGF-1. This pool was then concentrated to a volume of 50 ml in an Amicon pressure cell using a YM2 membrane (2,000 m.w. cut off). In order to remove the ammonium salt, the concentrated, purified monomer pool was diluted 10-fold with two 0.1M acetic acid and reconcentrated. This dilution and concentration step was repeated twice. A final volume of 45 ml was removed from the pressure cell and the filter was washed with two 0.1M acetic acid washes totaling 5 ml. The first 45 ml was passed through a Corning 0.22 micron filter, and then the 5 ml collected from the filter wash was also filtered through the same filter and combined with the 45 ml to bring the total volume of final purified authentic IGF-1 to 50 ml. The amount of concentrated IGF-1 (Table II) was determined at 453 mg by HPLC for a yield of 94% for the concentration step and a total yield of 46% for the entire purification process.

To ensure that ammonia was being removed by this process, the level of ammonia in each filtrate collected during the concentration and dilution series was determined using an ammonia combination electrode (Corning, Medford, Mass.). A standard curve was generated with known ammonia concentrations. The ammonia concentrations were calculated at 53 mM for the gel filtration buffer and 42 mM for the first filtrate obtained from the initial concentration step. Subsequent filtrates from the series of 10-fold dilutions and concentrations were calculated at 4.6, 0.016, and 0.001 mM ammonia.

EXAMPLE 3: CHARACTERIZATION OF PICHIA-PRODUCED IGF-1 PURIFIED FROM FERMENTATION BROTH

The eluate pools of purified IGF-1 obtained after the second HIC step of several repetitions of the procedure described above were concentrated in 0.1M acetic acid by diafiltration, as described in Example 2E. Typical samples of intact, monomeric, correctly-folded IGF-1, purified as described above from broth of strain G+IMB204S14 and strain M+IMB206S1 were characterized and quantitated by HPLC, gel filtration chromatography, SDS-PAGE, immunoblot, amino acid composition and amino acid sequence analyses.

A. HPLC Analysis

1. Protocol

A Waters (Medford, Mass.) 600 solvent delivery system, Waters Model 481 Lambda Max variable wavelength detector, Wisp 710B auto-injector and a Schimadzu Crom-Pac (Cole Scientific, Moorepark, Calif.) integrator constituted the HPLC system. A Vydac C4 column (0.46×5 cm) with a guard column was used to resolve components of the *Pichia pastoria*-produced IGF-1 preparations. Samples obtained during the purification process and samples of the final purified preparation of IGF-1 were loaded onto the column at a flow rate of 1 ml/min and were eluted in a trifluoroacetic acid (TFA)/acetonitrile gradient. The eluant was prepared by using mobile phase A (0.1% TFA) to dilute mobile phase B (95% acetonitrile, 5% water, 0.1% TFA). A 1%/minute gradient of 25% to 42% mobile phase B was passed through the column during a period of 17 minutes at a flow rate of 1 ml/minute to elute the material that had been loaded onto the column. The column was then regenerated with 100% mobile phase B at a flow rate of 2 ml/minute for 4 minutes followed by 25% mobile phase B for 4 minutes at 2 ml/minute. The flow rate was then reduced to 1 ml/minute and the column was equilibrated for 2 minutes before reinjection with another sample to be analyzed. The detector was set at 0.05 absorbance units full scale (AUFS) and a wavelength of 215 nm was used for maximum sensitivity.

In order to quantitate the levels of Pichia-produced IGF-1 by HPLC, known amounts of standard IGF-1 (Amgen) (0.5–5.0 μg) were injected onto the HPLC column and the area under the corresponding peaks in the chromotograms was measured. A standard curve was generated by plotting area versus μg of IGF-1 loaded onto the HPLC column. A conversion factor for use in converting the area under HPLC chromatogram peaks to IGF-1 was calculated from the standard curve. When the detector was set at 0.05 AUFS and wavelength of 215 nm, the conversion factor varied from 350 units/μg to 405 units/μg of IGF-1 injected onto the column. Using this information, it was possible to determine the concentration of correctly folded, intact, monomeric IGF-1 present in a broth or purification sample by measuring the area under the corresponding peak on the chromatogram from HPLC analysis of the sample. This conversion factor was also used to estimate the approximate concentration of other IGF-1 species as well. However, the absolute concentrations of each of these other species may vary depending on differences in their specific conversion factors.

2. Analysis of purified sample

Several dilutions of purified IGF-1 were analyzed by HPLC. The equivalents of 5, 2, 1, 0.5, 0.2, and 0.1 μl of the concentrated purified IGF-1 were injected onto the C4 column. The area of the peak corresponding to intact, correctly-folded, monomeric IGF-1 in chromatograms from the analysis of 0.1- to 1-2 μl aliquots was directly proportional to the volume of the sample. Using an IGF-1 standard obtained from Amgen, a standard curve was generated and used to calculate a concentration of 8.2±1.4 mg/ml for the IGF-1 concentration of the purified preparation from broth of strain G+IMB204S14 and of 9.0±0.3 mg/ml for the IGF-1 concentration of the purified preparation from broth of strain M+IMB206S1.

Purity estimates of the IGF-1 preparation increased with decreasing volume of the purified material injected onto the HPLC column. The chromatogram of a 2-μl aliquot of sample purified from broth of G+IMB204S14 indicated that the preparation was 97.3% pure intact, correctly-folded IGF-1 monomer, with three minor contaminants, represented by a front shoulder peak (possibly misfolded IGF), a back shoulder peak (nicked IGF), and the multimer region peaks, comprising 0.9%, 0.4% and 1.4% of the preparation, respectively. Purity determination based on HPLC analysis of a 1-μl aliquot indicated that the preparation was 98.7% pure correctly-folded, intact IGF-1 monomer with no multimer present, whereas HPLC analysis of a 0.2-μl aliquot indicated that the preparation was 99.4% pure correctly-folded, intact IGF monomer. Because the multimer elutes from the HPLC column as a broad heterogeneous peak, it is difficult to estimate its presence by HPLC. However, 2 μl of the concentrated purified IGF-1 is equivalent to almost 15 μg of IGF-1. Therefore, it would be expected that low-level contaminants would be detected in HPLC analysis of a 2-μl aliquot of purified IGF-1.

The chromatogram of a 2-μl aliquot of sample purified from broth of strain M+IMBH206S1 indicated that the preparation was 97.3% pure authentic IGF-1 with 1.1% multimer, 0.73% nicked and 0.9% putative misfolded IGF-1. The estimated purity of the 0.1–0.5 μl aliquots was greater than 99%.

B. Gel Filtration Chromatography Analysis

1. Protocol

A Superdex 75 HR 10/30 gel filtration column (Pharmacia, Uppsala, Sweden) with a bed volume of 24 ml (10×300 mm) was used to characterize the final purified IGF-1. The HPLC system described above (see Example 3A) was modified for use with this column. The detector was set at a wavelength of 280 nm and a sensitivity of 0.05 AUFS. IGF-1-containing samples obtained during purification of IGF-1 from broth were loaded onto the column and a buffer containing 0.1 to 0.3M ammonium acetate, pH 6, was used at a flow rate of 0.5 ml/minute to separate the IGF-1 species by size.

2. IGF-1 Analyses a. IGF-1 purified from broth of strain G+IMB204S14: To estimate the actual level of IGF-1 multimer present in the purified IGF-1 preparation from broth of strain G+IMB204S14, 50 μl of the concentrated purified IGF-1 (approximately 250 μg), diluted to a volume of 200 μl with 0.3M ammonium acetate, pH 6, was analyzed by gel filtration chromatography. Integration of the two peaks corresponding to the two faster eluting contaminants (multimer IGF-1) indicated that the first peak (material eluting at 22.67 minutes which was presumably trimer) was 1.0% of the total area and the second peak (material eluting at 24.75 minutes which was presumably dimer) was 2.6% of the total area. The overall percentage of multimer in the purified preparation was calculated at 3.6%, and the percentage of monomer (third fastest eluting species in the chromatogram) was calculated at 94.9%. The material corresponding to these three peaks was collected and separately analyzed by HPLC (see protocol described in Example 3A).

From the HPLC chromatogram of material corresponding to the monomer peak in the gel filtration chromatogram, it was calculated that more than 95% of the IGF-1 monomer that was loaded onto the gel filtration column was recovered in the eluate. Approximately 19 μg of intact monomer IGF-1 from the gel filtration column was loaded onto the C4 column, and no multimer was detected in the HPLC chromatogram.

The multimer forms of IGF-1 that eluted from the gel filtration column as the two fastest eluting species were also analyzed by HPLC, but the multimer concentration was too low for detection on HPLC.

In order to analyze some of the multimer species that might be present in low amounts in the purified IGF-1, 200 μl of material from the first pool of eluate fractions from the first HIC step of the purification (see Example 2D) was subjected to gel filtration chromatography (as described above) since it contained a relatively high level of multimer. The material corresponding to the individual peaks was collected and separately analyzed by HPLC. HPLC chromatograms of the components of the first pool of eluate fractions from the first HIC step eluted from the gel filtration column at 22.7 minutes (trimer) and 24.8 minutes (dimer), respectively. Material that eluted at approximately 35.5 minutes from the gel filtration column was also analyzed by HPLC, but no peaks were detected in the HPLC chromatogram. Presumably, this is a small IGF-1 peptide that either binds too tightly to the C4 column, so that it was not removed in the elution gradient, or does not bind to C4 at all.

b. IGF-1 purified from broth of strain M+IMB206S1: The chromatogram from gel filtration chromatography analysis of 450 μg of the final preparation purified from broth of strain M+IMB206S1 showed that it contained 99.2% monomer and 0.8% multimer IGF-1. The chromatogram of a 200 μg of this preparation indicated that it consisted of 100% monomer.

C. SDS-PAGE and Immunoblot Analysis

1. Protocols a. SDS-PAGE i. Electrophoresis conditions: The tricine sodium dodecyl sulfate polyacrylamide gel electrophoresis (tricine SDS-PAGE) system [Schagger, H. and von Jagow, G. (1987) *Anal. Biochem.* 166:368], a system optimized for the separation of proteins ranging from 5 to 20 kDa, was used for electrophoretic analysis of IGF-1-containing samples. In brief, electrophoresis was conducted in the Mini-PROTEAN II (BioRad, Richmond, Calif.) vertical gel system. Separating gels were 13% T, 3% C, and the stacking gels were 4% T, 3% C. As defined by Schagger and von Jagow (supra), T denotes the total percentage concentration of both monomers (acrylamide and bisacrylamide), and C denotes the percentage concentration of the cross-linker relative to the total concentration T.

Electrophoresis samples were prepared by placing them in a boiling water bath for 2–3 minutes after adding sample buffer components to the following concentrations: 2% SDS, 12% glycerol, 50 mM Tris HCl, pH 6.8, 0.0025% Coomassie Brilliant Blue G, and 0.001% pyronin Y. In addition, the disulfide bonds of some samples were reduced by the inclusion of 100 mM dithiothreitol (DTT) in the sample buffer. A constant volume of sample buffer was added to each well of the gels, including the "blank" lanes. Electrophoresis was conducted at a maximum 100 volts until the tracking dyes reached the bottom of the gels. The gels were then processed for either Western blot analysis or for protein staining.

ii. Fixing and Coomassie-staining tricine gels: Protein visualization by Coomassie staining was conducted by incubating the gels in 50% ethanol, 10% acetic acid, 5% TCA and 200 mg/L Coomassie Brilliant Blue R-250 for 30 minutes. Due to the ethanol contained in this solution, the gels partially dehydrated after Coomassie staining. Therefore, following staining, the gels were rehydrated in 10% ethanol, 7% acetic acid, 1% TCA and 50 mg/L Coomassie Brilliant Blue R-250. To covalently fix the proteins in the gels, the gels were incubated for 30 minutes in 10% glutaraldehyde. Following the final incubation, the gels were washed extensively with distilled water to remove the glutaraldehyde. The washing procedure typically involved soaking the gels in distilled water for two hours, during which time fresh water was added at least twice, followed by an overnight incubation of the gels in several volumes of distilled water.

b. Immunoblot: Purified protein and cell-free broth protein samples that were analyzed by immunoblot were first separated by tricine gel electrophoresis (see Example 3.C.1.a) and then electroblotted onto 0.1 $\mu$m nitrocellulose in a solution of Towbin buffer (25 mM Tris HCl, pH 8.3, 190 mM glycine, 20% methanol). Before electrotransfer, protein gels were equilibrated for 30 minutes in Towbin transfer buffer. Non-reduced gels were equilibrated in Towbin buffer containing 1% $\beta$-mercaptoethanol.

After the proteins were transferred onto nitrocellulose, the filter was incubated for one hour in blocking buffer (0.25% gelatin, phosphate-buffered saline, 0.05% Tween 20, 0.02% sodium azide). Rabbit anti-IGF-1 antisera 10A, generated against a C-terminal 'IGF-1-peptide, was diluted 1:2000 with blocking buffer and incubated with the filter overnight. The filter was washed with blocking buffer for an hour and incubated with $^{125}$I-Protein A (0.02 $\mu$Ci/ml) for 45 minutes. After one hour of washing with blocking buffer, the filter was air dried and exposed to X-ray film with an intensifying screen at $-75°$ C.

2. Analyses
a. SDS-PAGE
i. IGF-1 purified from broth of strain G+IMB204S14: Non-reduced and reduced samples of the purified IGF-1 containing 5, 2, 1, 0.5, 0.2, and 0.1 $\mu$g of IGF-1 as determined by amino acid composition analysis were subjected to electrophoresis, and Coomassie staining. The minimum amount of reduced or non-reduced IGF-1 that could be detected in Coomassie-stained SDS-PAGE gels was 0.2 $\mu$g. A single band corresponding to a protein that co-migrated with standard IGF-1 was visible in gels containing non-reduced and reduced samples (0.2, 0.5, 1 or 2 $\mu$g) of purified IGF-1. However, two bands, one corresponding to a protein that co-migrated with standard IGF-1 and one corresponding to a protein that migrated more slowly than standard IGF-1, were visible in the gels of the non-reduced and reduced 5-$\mu$g samples of IGF-1. The more slowly migrating protein in the non-reduced 5-$\mu$g sample was identified as a multimer of disulfide-bonded IGF-1 monomers. The amount of multimer present in the purified IGF-1 preparation was estimated at 4-10% of the total IGF-1 based on a visual comparison of the intensities of the bands corresponding to IGF-1 multimer and known amounts of purified IGF-1.

The faint band detected above the band corresponding to monomeric IGF-1 in gels of reduced 5 $\mu$g samples of purified IGF-1 migrated to the same position as does multimeric IGF-1. Additional SDS-PAGE analyses of reduced sample of purified IGF-1 have been conducted under more stringent reducing conditions, and this band was not detected. Furthermore, this band was present on the corresponding Western blot (see Example 3C2c) of reduced samples of purified IGF-1, indicating that it is a multimeric form of IGF-1. Therefore, this upper band is most likely the result of incomplete reduction of the IGF-1 prior to electrophoresis. Bands corresponding to proteins migrating more rapidly than monomer IGF-1, which would indicate the presence of nicked or degraded IGF-1, were not detected in the gel of the reduced samples. Because no other bands were seen on the reduced gel, the level of purity for the purified IGF-1 is most likely greater than 95%.

ii. IGF-1 purified from broth of strain M+IMB206S1: Aliquots of the preparation purified from broth of strain M+IMB206S1 containing 200, 500, 1000, and 2000 ng authentic IGF-1 were loaded into lanes of an SDS-PAGE gel. The non-reduced samples showed a faint band corresponding to multimer IGF-1 on the silver-stained gel; however, this species was barely visible in western blots of less than 2000 ng of the purified preparation. The level of multimer could not be determined from a silver-stained gel since the staining intensity was not proportional to the level of protein, especially for low level contaminants. Another band was seen just above the monomer band in the lanes of the silver-stained gel containing 1000 and 2000 ng of non-reduced IGF-1. This species was present at a level less than that of the multimer contaminant. The SDS-PAGE gel of the reduced samples did not show any contaminants except for a very light band at the multimer position in the lane containing 2000 ng of IGF-1.

b. Scanning densitometry: To more accurately determine the multimer concentration from the results of SDS-PAGE analyses of purified IGF-1, the gels of reduced and non-reduced samples of IGF-1 purified from broth of strain G+IMB204S14 were subjected to scanning densitometry using a Hoefer (San Francisco, Calif.) scanning densitometer at a fixed wavelength of 580 nm. Densitometer tracings were generated by scanning the gels of non-reduced 5-$\mu$g and 2-$\mu$g samples and reduced 5-$\mu$g and 2-$\mu$g samples. The two peaks in the tracing generated by scanning the gels of non-reduced samples correspond to multimer and monomer IGF-1, respectively. The small peaks in the densitometer tracings generated by scanning the gels of reduced samples of purified IGF-1 correspond to incompletely reduced IGF-1 multimer, whereas the large peaks in the same tracings correspond to reduced multimer plus monomeric IGF-1. The calculated areas for the monomer peaks corresponding to 0.2 up to 5 $\mu$g of purified, non-reduced IGF-1 were plotted against the amount of IGF-1 to establish a standard curve. The curve was linear between 0.2 to 2 $\mu$g of IGF-1. However, the peak corresponding to the multimer band in the gel containing 5 $\mu$g of non-reduced IGF-1 could still be used to calculate the amount of multimer present since the multimer in this lane represented less than 2 $\mu$g. The area for the 5 $\mu$g multimer peak was used to calculate an amount of 0.63 $\mu$g, which is equivalent to a multimer concentration of 12.7%. A multimer amount of 0.07 $\mu$g was calculated based on the area of the peak corresponding to a multimer in 2 $\mu$g of non-reduced IGF-1 which is equivalent to a multimer concentration of 3.4%. Tracings generated by scanning the gels of non-reduced samples of the purified preparation containing less than 2 $\mu$g of IGF-1 indicated that the material was 100% pure monomeric IGF-1. It should be noted that there was a high amount of background in the tracing generated by scanning the gels of non-reduced purified IGF-1, and this background was included in the area calculations for the multimer peaks. Thus, the values calculated for the multimer concentration of purified IGF-1 based on scanning densitometry are over-estimations of the actual concentration.

c. Immunoblot analysis of IGF-1 purified from broth of strain G+IMB204S14: Tricine SDS-PAGE gels of reduced and non-reduced samples of purified IGF-1 (0.1, 0.2, 0.5, 1, 2 and 5 μg of intact IGF-1 monomer based on HPLC analyses of purified IGF-1) were also subjected to immunoblotting. Estimates of IGF-1 multimer and monomer concentration based on immunoblot analyses are dependent on the relative binding of multimer and monomer to the polyclonal antisera used in the analyses, and evidence exists for a greater binding of antisera by multimer as compared to monomer IGF-1. Therefore, immunoblot analysis of purified IGF-1 is a more sensitive method for the detection of IGF-1 multimer than SDS-PAGE. However, when estimating the amount of multimer in the purified IGF-1 by immunoblot analysis, it is necessary to keep in mind the possible effects of relative antibody binding.

In the immunoblot of non-reduced samples of purified IGF-1, bands corresponding to multimer IGF-1 were detected in lanes containing Amgen IGF-1 standard as well as in the 5-, 2- and 1- μg samples of purified IGF-1. The multimer band in the lane containing 2 μg of purified IGF-1 appeared to be similar in intensity to the monomer band in the lane containing 0.1 μg of purified IGF-1 (which would equate to a multimer level of 5%) and of much less intensity than the monomer band in the lane containing 0.2 μg of purified IGF-1 (multimer level <10%). Visual estimates of the IGF-1 multimer content of the purified IGF-1 by western blot analysis of non-reduced samples (5–10%) compare well with values obtained by visual estimation of Coomassie-stained SDS-PAGE gels of the non-reduced samples.

Similar to the Coomassie-stained SDS-PAGE gels of reduced samples of purified IGF-1, the immunoblot of the reduced samples also showed the incomplete reduction in the 5 μg sample. Most importantly, all the bands that appeared in the Coomassie-stained SDS-PAGE gels of purified IGF-1 were present in the immunoblots of the samples. This indicates that there are no non-IGF-1 contaminants present in the purified preparation, and that the only readily measurable contaminant present in the purified IGF-1 is multimeric IGF-1.

D. Summary of HPLC, Gel Filtration chromatography, SDS-PAGE and Immunoblot Analyses of IGF-1 purified from broth of strain G+IMB204S14

The percentages of IGF-1 multimer in the purified IGF-1 preparation determined by HPLC (1.4%), gel filtration chromatography (3.6%), SDS-PAGE (4–10%), immunoblot (5–10%) and densitometry of Coomassie-stained SDS-PAGE gels (3.4–12.7%) all seem to be in fairly close agreement considering the low levels of multimer present in the preparation. Because 250 μg of IGF-1 was loaded onto the gel filtration column, this technique was probably the most accurate for determining the multimer levels of the purified IGF-1. Furthermore, there is the possibility that sample preparation for SDS-PAGE analysis caused aggregation of some of the monomeric IGF-1 in the purified preparation resulting in higher estimates of the multimer level. No such sample preparation was performed for gel filtration chromatography. No non-IGF-1 protein contaminants were detected when the stained gels and immunoblots of samples of the purified IGF-1 were compared.

Although multimeric IGF-1 could be identified by a variety of techniques used to measure purity of the IGF-1 preparation, the nicked and misfolded forms of IGF-1 were differentiated and detected only by HPLC. The percentage of nicked IGF-1 was measured to be about 0.4% by HPLC, and 0% by SDS-PAGE and immunoblot analysis of reduced, purified IGF-1. HPLC analysis also showed a contaminant appearing as a front shoulder of the peak corresponding to intact, correctly-folded, monomeric IGF-1. This contaminant was present at a level of 0.9%, and is presumed to be misfolded form(s) of IGF-1.

E. Amino Acid Analysis

1. Protocol

Purified IGF-1 was acid hydrolyzed and the resultant amino acids characterized on a Beckman (Palo Alto, Calif.) 6300 Amino Acid Analyzer. To acid hydrolyze IGF-1 protein, carefully measured volumes of purified IGF-1 solution were added to 6×50 mm glass tubes and dried in a Savant (Farmingdale, N.Y.) Speed Vac. These tubes were placed in a reaction flask containing 6N HCl. Oxidation was minimized by applying a vacuum and sealing the flask. The flask was placed overnight in a 110° C. oven, and the protein was hydrolyzed by the hot HCl vapors.

Following hydrolysis, the reaction flask was cooled to room temperature, and the hydrolysis tubes were removed. Any HCl that may have condensed in the tubes was removed by drying in a Speed Vac. The free amino acids were dissolved in a minimum of 100 μl Beckman Amino Acid Sample Dilution Buffer, Na-S, for loading in the 50-μl loop of the analyzer. A Nelson (Cupertino, Calif.) 3000 Series Chromatography Data System was used for quantitation by comparing the integrated chromatograms of amino acid standard solutions and the resuspended, hydrolyzed samples.

2. Analyses a. IGF-1 purified from broth of strain G+IMB204S14: A protein concentration of 5.15 mg/ml was determined from eight separate analyses of purified IGF-1 using norleucine as an internal standard. A standard deviation of 0.26 mg/ml was also calculated. Therefore, 186 to 206 mg of protein was contained in the total volume of 38 ml of purified IGF-1. Table III shows the estimated and actual amino acid ratios. The values calculated for the numbers of cys, met, and tyr residues were all lower than the actual values due to oxidative destruction of these amino acids under conditions of hydrolysis. The higher value calculated for the number of threonine residues was most likely due to peak integration errors resulting from incomplete resolution of this residue and the adjacent serine residue. These deviations are within the expected limits of this method.

b. IGF-1 purified from broth of strain M+IMB206S1: Amino acid composition analysis was performed on the final IGF-1 purified from broth of strain M+IMB206S1 and a concentration of 8.4 mg/ml was calculated. Table IV shows the amino acid ratios estimated for the purified IGF-1 and the actual published amino acid ratios for human IGF-1. The estimated and published ratios are in close agreement, and slight deviations in the estimated and published compositions are within the expected limits of this analysis.

TABLE IV

IGF-1 Purified from broth of Strain M+IMB206S1 Amino Acid Composition Analysis Data

| Amino Acid | Published Composition[a] | Experimental |
|---|---|---|
| Asp (+ Asn) | 5 | 5.8 |
| Thr | 3 | 3.1 |
| Ser | 5 | 4.9 |
| Glu (+ Gln) | 6 | 6.9 |
| Pro | 5 | 3.0 |
| Gly | 7 | 7.4 |
| Ala | 6 | 6.8 |
| Cys | 6 | 5.5 |
| Val | 3 | 2.6 |
| Met | 1 | 0.9 |
| Ile | 1 | 0.66 |
| Leu | 6 | 7.1 |
| Tyr | 3 | 2.1 |
| Phe | 4 | 3.6 |
| His | 0 | 0 |
| Lys | 3 | 3.3 |
| Arg | 6 | 6.7 |
| Trp | 0 | |

[a] Derived from nucleotide sequence published by Rotwein et al. (supra).

TABLE III

AMINO ACID COMPOSITION ANALYSIS OF IGF-1 PURIFIED FROM BROTH OF STRAIN G+IMB204S14

| Amino Acids | Published Compositions[a] | Injections #1 | #2 | #3 | #4 | #5 | #6 | #7 | #8 | Estimated Average of Tests 1–8 |
|---|---|---|---|---|---|---|---|---|---|---|
| Asp (+ Asn) | 5 | 5.5 | 5.1 | 5.1 | 5.1 | 5.2 | 5.0 | 5.1 | 5.1 | 5.1 |
| Thr | 3 | 5.2 | 5.2 | 4.8 | 5.4 | 4.0 | 4.0 | 4.1 | 4.2 | 4.6 |
| Ser | 5 | 4.6 | 4.1 | 4.6 | 4.1 | 4.2 | 4.2 | 4.3 | 4.4 | 4.3 |
| Glu (+ Gln) | 6 | 6.9 | 6.6 | 6.7 | 6.6 | 6.1 | 6.5 | 6.5 | 6.5 | 6.5 |
| Pro | 5 | 5.0 | 5.7 | 0.0 | 6.1 | 0.0 | 5.7 | 6.0 | 6.0 | 4.3 |
| Gly | 7 | 7.5 | 6.8 | 6.5 | 6.8 | 6.7 | 6.7 | 6.8 | 6.7 | 6.8 |
| Ala | 6 | 6.4 | 6.4 | 6.8 | 6.5 | 6.5 | 6.4 | 6.4 | 6.4 | 6.5 |
| Cys | 6 | .0 | 0.0 | 0.0 | 0.0 | 1.4 | 1.7 | 1.9 | 2.0 | .9 |
| Val | 3 | 2.9 | 2.7 | 2.6 | 2.5 | 2.4 | 2.2 | 2.2 | 2.2 | 2.5 |
| Met | 1 | .0 | 0.0 | 0.0 | .1 | .3 | .1 | .1 | .1 | .1 |
| Ile | 1 | .4 | .4 | .3 | .3 | .4 | .4 | .4 | .4 | .4 |
| Leu | 6 | 6.0 | 6.0 | 6.0 | 6.0 | 6.0 | 6.0 | 6.0 | 6.0 | 6.0 |
| Tyr | 3 | 1.9 | 2.3 | 1.9 | 1.8 | 2.1 | 1.9 | 1.6 | 1.6 | 1.9 |
| Phe | 4 | 3.6 | 3.9 | 3.5 | 3.5 | 3.9 | 3.8 | 3.5 | 3.5 | 3.6 |
| His | 0 | .2 | 0.0 | .2 | .2 | .5 | .4 | 0.0 | .4 | .2 |
| Lys | 3 | 3.6 | 3.0 | 3.0 | 2.9 | 3.5 | 3.0 | 2.9 | 2.9 | 3.1 |
| Arg | 6 | 5.0 | 5.0 | 5.4 | 5.4 | 5.6 | 5.4 | 5.5 | 5.5 | 5.4 |
| (Trp) | 0 | | | | | | | | | |

[a] Derived from nucleotide sequence published by Rotwein, et al., supra.

F. Protein Sequence Analysis

1. IGF-1 Purified from broth of strain G+IMB204S14

To determine the entire amino acid sequence of the purified IGF-1, samples of this material were loaded directly onto an Applied Biosystems (Foster City, Calif.) 470/120 Gas Phase protein sequencer. Sequencing was performed according to the method described by Hunkapiller and Hood [Science 219:650 (1983)]. The material was sequenced from the N-terminal amino acid through as much of the remainder of the protein sequence as possible. This analysis generated the sequence of the first 59 residues of the purified protein.

Because the amino acid at residue 59 is a methionine residue, and cyanogen bromide cleaves proteins after methionine residues, it was possible to isolate the peptide consisting of the C-terminal 11 amino acids (residues 60–70) of purified IGF-1 for use in completing the protein sequence analysis of the purified material. The C-terminal 11 amino acids of the purified IGF-1 were obtained as a peptide fragment isolated from cyanogen bromide-treated IGF-1 by HPLC, using the same C4 column as described in Example 3A1. This fragment was loaded onto the protein sequencer to generate the sequence of the C-terminal amino acids (amino acids 60–70).

Every residue of the material purified according to the invention process has been positively identified except for the cysteines. These residues are identified by the complete absence of any residue in that cycle. The entire sequence corresponded to authentic human IGF-1.

2. IGF-1 purified from broth of strain M+IMB206S1

Amino terminal sequence analysis of IGF-1 purified from broth of strain M+IMB206S1 revealed that the first 30 amino acids were identical to the N-terminal sequence of human IGF-1.

The invention has been described in detail with respect to certain particular embodiments thereof, but reasonable variations and modifications, within the spirit and scope of the present disclosure, are contemplated by the present disclosure and the appended claims.

That which is claimed is:

1. Method for the purification of monomeric, intact, correctly-folded insulin-like growth factor-1 peptide (IGF-1) from medium containing IGF-1 peptides, said method comprising:

(a) contacting said medium with a sufficient quantity of first cation exchange material under conditions suitable to adsorb at least about 95% of total IGF-1 from said medium, (b) eluting the adsorbed IGF-1 from the IGF-1-containing cation exchange material of step (a) by contacting said cation exchange material with a sufficient quantity of a solvent system which has a sufficiently high pH or ionic strength so as to displace aberrant substantially all of said IGF-1 from said cation exchange material, (c) contacting the IGF-1-containing fractions of the eluate of step (b), in a suitable solvent system, with a sufficient quantity of a first hydrophobic interaction chromatography matrix under conditions suitable to adsorb in the range of about 95 up to 100% of said IGF-1 from said eluate, (d) eluting the adsorbed IGF-1 from said first hydrophobic interaction chromatography matrix by contacting said matrix first with in the range of about 1 up to 10 volumes, relative to the volume of matrix, of a buffer system having a sufficiently low conductivity so as to displace aberrant IGF-1 peptides from said matrix, without displacing significant quantities of the intact, monomeric, correctly-folded form of adsorbed IGF-1 from said first hydrophobic interaction chromatography matrix, followed by contacting said matrix with in the range of about 1 up to 10 volumes, relative to the volume of matrix, of a buffer system having an elevated pH, wherein said elevated pH is sufficiently high so as to displace substantially all of the remaining adsorbed forms of IGF-1 from said matrix, (e) contacting the fractions eluted according to step (d) employing said buffer system having an elevated pH which contain, as the predominant form of IGF-1, intact, monomeric, correctly-folded IGF-1, wherein said contacting is carried out with a sufficient quantity of a second cation exchange matrix and under conditions suitable to adsorb in the range of about 95 up to 100% of total IGF-1 from said eluate, (f) eluting the adsorbed IGF-1 from said second cation exchange matrix by contacting said matrix with at least 1 volume, relative to the volume of matrix, of a buffer system having a sufficient ionic strength so as to differentially displace substantially all of the IGF-1 peptides from said matrix, (g) contacting the intact, monomeric, correctly-folded IGF-1-containing fractions of the eluate from step (f), in a suitable solvent system, with either, (1) a sufficient quantity of a second hydrophobic interaction chromatography matrix under conditions suitable to adsorb in the range of about 95 up to 100% of all forms of IGF-1 from said eluate, or, (2) a sufficient quantity of a gel filtration chromatography matrix having suitable pore size to effect resolution of the intact, monomeric correctly-folded form of IGF-1 from substantially all multimeric forms of IGF-1, and (h) (1) after step (g) (1) eluting the adsorbed IGF-1 from said second hydrophobic interaction chromatography matrix by contacting said matrix with in the range of about 1 up to 10 volumes, relative to the volume of matrix, of a buffer system having a sufficiently low conductivity so as to displace substantially all forms of IGF-1 other than the intact, monomeric, correctly-folded form of IGF-1 from said matrix, without displacing significant quantities of the intact, monomeric, correctly-folded form of adsorbed IGF-1 from said second hydrophobic interaction chromatography matrix, followed by contacting said matrix with in the range of about 1 up to 10 volumes, relative to the volume of matrix, of a buffer system having a sufficiently high pH so as to displace substantially all of the remaining absorbed IGF-1 from said matrix or, (2) after step (g) (2) eluting said gel filtration chromatography matrix with a sufficient quantity of elution buffer so as to cause the intact, monomeric correctly-folded form of IGF-1 to be resolved from said multimeric forms of IGF-1.

2. A method according to claim 1 wherein said medium contains at least 0.01 grams of IGF-1 peptides per liter of said medium.

3. A method according to claim 1 wherein said first cation exchange matrix is a strong cation exchange matrix capable of having a high flow rate.

4. A method according to claim 3 wherein said first cation exchange matrix is selected from carboxymethylated or sulfonated cation exchange media.

5. A method according to claim 4 wherein said first cation exchange matrix is a sulfylpropylated cellulose matrix.

6. A method according to claim 3 wherein the contacting contemplated by step (a) is carried out at a temperature in the range of about 2° up to 30° C.

7. A method according to claim 3 wherein the contacting contemplated by step (a) is carried out by passing the medium containing IGF-1 through a column containing said first cation exchange material.

8. A method according to claim 7 wherein, prior to step (b), said matrix is contacted with in the range of about one up to five column volumes, relative to the volume of matrix, of a dilute, weak acid solution, followed by in the range of about zero up to six column volumes, relative to the volume of matrix, of a buffered solution of a dilute, weak acid having a pH of 5 and containing 0.2M sodium chloride.

9. A method according to claim 8 wherein the dilute, weak acid is an acetic acid or phosphoric acid solution.

10. A method according to claim 9 wherein about two volumes of said dilute, weak acid solution are employed; wherein said dilute, weak acid solution is a 0.02M acetic acid solution; wherein about four volumes of said buffered solution having a pH of 5 and containing 0.2M sodium chloride are employed; and wherein said buffered solution is a 0.02M sodium acetate solution having a pH of 5 and containing 0.2M sodium chloride.

11. A method according to claim 1 wherein suitable solvent systems for the step (b) elution are buffered solutions of a weak, dilute acid having a pH of about 5.5 and containing about 1.0M sodium chloride.

12. A method according to claim 11 wherein, in the elution of IGF-1 from the first cation exchange matrix, in the range of about 3 up to 10 volumes, per volume of said matrix, of said suitable solvent system is employed.

13. A method according to claim 11 wherein said suitable solvent system for the step (b) elution is a 0.02M sodium acetate solution having a pH of 5.5 and containing 1.0M sodium chloride.

14. A method according to claim 13 wherein the IGF-1-containing eluate fractions of step (b) is treated, prior to step (c), by diluting said eluate with a sufficient volume of a buffered salt-containing solution, pH 4.5, so as to render the salt concentration of the diluted eluate in the range of about 0.2 up to 2M, and the pH of the diluted eluate about 4.5.

15. A method according to claim 1 wherein the contacting contemplated by step (c) is carried out by passing the medium containing IGF-1 through a column containing said first hydrophobic interaction chromatography matrix; wherein the contacting contemplated by step (g) (1) is carried out by passing the medium containing IGF-1 through a column containing said second hydrophobic interaction chromatography matrix; and wherein said first and said second hydrophobic interaction chromatography matrices are each independently selected from an alkyl- or aryl-substituted hydrophobic interaction chromatography matrix.

16. A method according to claim 15 wherein said hydrophobic interaction chromatography matrix is a butyl-, octyl-, or phenyl-substituted hydrophobic interaction chromatography matrix.

17. A method according to claim 16 wherein said hydrophobic interaction chromatography matrix is a butyl-substituted, poly(methacrylate)-supported HIC matrix.

18. A method according to claim 15 wherein the contacting contemplated by steps (c) and (g) (1) are each independently carried out at a temperature in the range of about 15° up to 30° C.

19. A method according to claim 15 wherein said first hydrophobic interaction chromatography matrix is a non-silica-based matrix, and is regenerated by four sequential washes comprising:
in the range of 3–10 column volumes of water,
in the range of 3–10 column volumes of a 0.5N sodium hydroxide solution,
in the range of 3–10 column volumes of a 50% aqueous methanol solution, and finally in the range of 3-10 column volumes of water, and thereafter, the column was equilibrated with in the range of 5-10 column volumes of an ammonium sulfate-containing acetate/phosphate buffer having a pH of 4.5.

20. A method according to claim 1 wherein the elution of adsorbed IGF-1 from the IGF-1-containing matrix according to steps (d) and (h) (1) comprises, in each step, contacting said matrix
  (i) first with a linear gradient of a buffered solution having a pH of about 4.5 in a quantity sufficient to produce a substantially salt-free eluate, then
  (ii) with a linear gradient of a substantially salt-free buffered solution having an initial pH of about 4.5 in a quantity sufficient to raise the pH of said eluate up to about 6.5.

21. A method according to claim 1 wherein a portion of the eluate of step (d) eluted at elevated pH is again subjected to steps (c) and (d), and the intact, monomeric, correctly-folded IGF-1-containing eluates of both step (d) elutions are combined before proceeding with step (f).

22. A method according to claim 1 wherein the contacting contemplated by step (e) is carried out by passing the medium containing IGF-1 peptides through a column containing said second cation exchange material; and wherein said second cation exchange matrix is a strong cation exchange matrix capable of high resolution.

23. A method according to claim 22 wherein the pH of the eluate of step (d) is adjusted to about 4.5, and said eluate is diluted with at least 1 volume of water or a low conductivity buffer prior to the contacting contemplated by step (f).

24. A method according to claim 22 wherein said second cation exchange matrix is selected from carboxymethylated or sulfonated cation exchange media.

25. A method according to claim 24 wherein said second cation exchange matrix is a sulfylmethyl agarose.

26. A method according to claim 22 wherein the contacting contemplated by step (e) is carried out at a temperature in the range of about 2° up to 30° C.

27. A method according to claim 22 wherein said second cation exchange matrix is activated/regenerated by four sequential washes comprising:
  in the range of 3-10 column volumes of water,
  in the range of 3-10 column volumes of a 0.5N sodium hydroxide solution,
  in the range of 3-10 column volumes of a 50% aqueous methanol solution, and finally
  in the range of 3-10 column volumes of water, and thereafter, the column was equilibrated with
  in the range of 3-5 column volumes of 0.5M sodium acetate, pH 4.5, and
  in the range of 10-20 column volumes of a 0.05M sodium acetate, pH 4.5.

28. A method according to claim 22 wherein, prior to step (f), said second cation exchange matrix is contacted with in the range of about 1 up to 5 volumes, relative to the volume of matrix, of a dilute buffer of a weak acid.

29. A method according to claim 28 wherein the dilute buffer of a weak acid, is an acetic acid or phosphoric acid based buffer solution.

30. A method according to claim 29 wherein said dilute buffer of a weak acid comprises a 0.05M sodium acetate solution having a pH of 4.5.

31. A method according to claim 1 wherein suitable solvent systems for the step (f) elution comprise a sodium chloride gradient in a sodium acetate buffer, pH 5.5.

32. A method according to claim 31 wherein, in the elution of IGF-1 from the second cation exchange matrix, in the range of about 3 up to 15 volumes, per volume of said matrix, of said suitable solvent system is employed.

33. A method according to claim 32 wherein said sodium chloride gradient is provided by combining, as a linear gradient, a first solvent system and a second solvent system;
  wherein said first solvent system comprises a 0.05M sodium acetate solution, pH 5.5, and
  wherein said second solvent system comprises a 0.05M sodium acetate/0.3M sodium chloride solution, pH 5.5.

34. A method according to claim 1 wherein the IGF-1-containing eluate of step (f) is treated, prior to step (g) (1), by diluting said eluate with a sufficient volume of a buffered salt-containing solution, pH 4.5, so as to render the salt concentration of the diluted eluate in the range of about 0.2 up to 2M, and the pH of the diluted eluate about 4.5.

35. A method according to claim 15 wherein said second hydrophobic interaction chromatography matrix is a non-silica based matrix, and is regenerated by four sequential washes comprising:
  in the range of 3-10 column volumes of water,
  in the range of 3-10 column volumes of a 0.5N sodium hydroxide solution,
  in the range of 3-10 column volumes of a 50% aqueous methanol solution, and finally
  in the range of 3-10 column volumes of water, and thereafter, the column was equilibrated with in the range of 5-10 column volumes of an ammonium sulfate-containing acetate/phosphate buffer having a pH of 4.5.

36. A method according to claim 1 wherein a portion of the eluate of step (h) (1) eluted at elevated pH is again subjected to steps (g) (1) and (h) (1) and the intact, monomeric, correctly-folded IGF-1-containing eluates of both step (h) (1) elutions are retained.

37. Method for the purification of monomeric, intact, correctly-folded insulin-like growth factor-1 (IGF-1) peptide from medium containing IGF-1 peptides, wherein said medium containing IGF-1 is the substantially cell-free fermentation broth from a high cell density yeast fermentation operation, and wherein said yeast are transformed with at least one DNA fragment comprising, in the direction of transcription, the following DNA sequences:
  (i) a promoter region of a methanol-responsive gene of *P. pastoris*,
  (ii) a DNA sequence encoding a polypeptide consisting of:
    (a) The *S. cerevisiae* AMF pre-pro sequence, including the processing site: lys-art and
    (b) an insulin-like growth factor-1 (IGF-1) peptide; and
  (iii) a transcription terminator functional in *P. pastoris*, wherein said DNA sequences are operationally associated with one another for transcription of the sequences encoding said polypeptide, said method comprising:
    (a) diluting said IGF-1-containing medium with a low conductivity buffered medium having the same pH as the media used to equilibrate the cation exchange matrix employed in step (b) below, (b) contacting said medium with a sufficient quantity of a sulfylpropylate cation exchange media under conditions suitable to adsorb at least about 95% of said IGF-1 from said medium; wherein at least 0.05 liters, per gram of IGF-1 in said medium, of said cation exchange material are employed; and wherein said contacting is carried out at a temperature in the range of about 2° up to 30° C., (c) contacting the IGF-1-containing cation exchange material with at least about 2 volumes, per volume of said cation exchange material, of a 0.02M acetic acid solution, followed by about four volumes of a 0.02M sodium acetate solution having a pH of 5 and containing 0.2M sodium chloride, (d) eluting the adsorbed IGF-1 from said IGF-1-containing cation exchange matrix material of step (c) by contacting said matrix material with a sufficient quantity of a solvent system comprising a 0.02M sodium acetate solution having a pH of 5.5 and containing 1.0M sodium chloride, (e) contacting the IGF-1-containing eluate of step (d) with a sufficient volume of a buffered ammonium sulfate-containing solution, pH 4.5, so as to render the ammonium sulfate concentration of the eluate in the range of about 0.4 up to 0.8M, and the pH of the diluted eluate about 4.5, (f) contacting the product of step (e) with a sufficient quantity of a first hydrophobic interaction chromatography matrix under conditions suitable to adsorb in the range of about 95 up to 100% of said IGF-1 from said eluate, wherein said first hydrophobic interaction chromatography matrix is a butyl-substituted, poly(methacrylate)-supported hydrophobic interaction chromatography matrix; wherein at least about 0.05 liters, per gram of IGF-1 in said medium, if said first hydrophobic interaction chromatography matrix are employed; and wherein said contacting is carried out at a temperature in the range of about 20° up to 25° C., (g) eluting the adsorbed IGF-1 from said first hydrophobic interaction chromatography matrix by contacting said matrix:
  (1) first with a quantity of a linear gradient of a buffered solution having a pH of about 4.5 sufficient to produce a substantially ammonium sulfate-free eluate, then
  (2) with a quantity of a linear gradient of a substantially ammonium sulfate-free buffered solution having an initial pH of about 4.5 sufficient to raise the pH of said eluate up to about 6.5, (h) contacting at least a portion of the eluate fractions obtained in step (g) (2) with a sufficient additional quantity of said first hydrophobic interaction chromatography matrix under conditions suitable to adsorb in the range of about 95 up to 100% of residual quantities of IGF-1 from said eluate; wherein at least about 0.05 liters, per gram of IGF-1 in said medium, of said first hydrophobic interaction chromatography resin are employed; and wherein said contacting is carried out at a temperature in the range of about 20° up to 25° C.

(i) eluting the adsorbed IGF-1 from said first hydrophobic interaction chromatography matrix by contacting said matrix:
  (1) first with a quantity of a linear gradient of a buffered solution having a pH of about 4.5 sufficient to produce a substantially ammonium sulfate-free eluate, then
  (2) with a quantity of a linear gradient of a substantially ammonium sulfate-free buffered solution having an initial pH of about 4.5 sufficient to raise the pH of said eluate up to about 6.5, (j) contacting those portions of the combined eluate from steps (g) (2) and (i) (2) which contain, as the predominant form of IGF-1, intact, monomeric, correctly-folded IGF-1, wherein said contacting is carried out with a sufficient quantity of a second cation exchange matrix material and under conditions suitable to adsorb in the range of about 95 up to 100% of said IGF-1 from said eluate; wherein said matrix comprises a sulfylmethylated agarose matrix; wherein at least 0.05 liters, per gram of IGF-1 in said medium, of said cation exchange material are employed; and wherein said contacting is carried out at a temperature in the range of about 2° up to 30° C., (k) contacting the IGF-1-containing second cation exchange matrix material with at least one, up to about five volumes, per volume of said cation exchange material, of a 0.05M sodium acetate solution, pH 4.5, (l) eluting the IGF-1 from said second cation exchange matrix material by contacting said matrix material with at least five volumes, relative to the volume of matrix, of a sodium chloride gradient, which is provided by combining, as a linear gradient, a first solvent system and a second solvent system;

wherein said first solvent system comprises a 0.05M sodium acetate solution, pH 5.5, and wherein said second solvent system comprises a 0.05M sodium acetate/0.3M sodium chloride solution, pH 5.5, (m) either
  (1) diluting the intact, monomeric, correctly-folded IGF-1 containing fractions of the eluate of step (1) with at least one volume of a buffered ammonium sulfate-containing solution, pH 4.5, so as to render the ammonium sulfate concentration of the eluate in the range of about 0.2 up to 2.0M and the pH of the diluted eluate about 4.5, and contacting the diluted eluate with a sufficient quantity of a second hydrophobic interaction chromatography matrix under conditions suitable to adsorb in the range of about 95 up to 100% of said IGF-1 from said eluate; wherein said second hydrophobic interaction chromatography matrix is a butyl-substituted hydrophobic interaction chromatography matrix; wherein at least about 0.05 liters, per gram of IGF-1 in said medium, of said second hydrophobic interaction chromatography matrix are employed; and wherein said contacting is carried out at a temperature in the range of about 20° to 25° C. or,
  (2) contacting the intact, monomeric, correctly-folded IGF-1-containing fractions of the eluate from step (1), with a sufficient quantity of a gel filtration chromatography matrix having suitable pore size to effect resolution of the intact, monomeric correctly-folded form of IGF-1 from substantially all multimeric forms of IGF-1, and (n)

(1) after step (m) (1) eluting the adsorbed IGF-1 from said second hydrophobic interaction chromatography matrix by contacting said matrix:
  (i) first with a quantity of a linear gradient of a buffered solution having a pH of about 4.5 sufficient to produce a substantially ammonium sulfate-free eluate, then
  (ii) with a quantity of a linear gradient of a substantially ammonium sulfate-free buffered solution having an initial pH of about 4.5 sufficient to raise the pH of said eluate up to about 6.5, or
(2) after step (m) (2) eluting said gel filtration chromatography matrix with a sufficient quantity of elution buffer so as to cause the intact, monomeric correctly-folded form of IGF-1 to be resolved said multimeric forms of IGF-1.

38. A method according to claim 37 wherein a portion of the eluate of step (n) (1) eluted at elevated pH is again contacted with said hydrophobic interaction chromatography matrix and eluted according to step (n) (1), and the intact, monomeric, correctly-folded IGF-1-containing eluates of both step (n) (1) elutions are retained.

39. Method for the purification of monomeric, intact, correctly-folded insulin-like growth factor-1 peptide (IGF-1) from medium containing IGF-1 peptides, said method comprising:
  (a) contacting said medium with a sufficient quantity of first cation exchange material under conditions suitable to adsorb at least about 95% of total IGF-1 from said medium,
  (b) eluting the adsorbed IGF-1 from the IGF-1-containing cation exchange material of step (a) by contacting said cation exchange material with a sufficient quantity of a solvent system which has a sufficiently high pH or ionic strength so as to displace substantially all of said IGF-1 from said cation exchange material,
  (c) contacting the IGF-1-containing fractions of the eluate of step (b), in a suitable solvent system, with a sufficient quantity of a first hydrophobic interaction chromatography matrix under conditions suitable to adsorb in the range of about 95 up to 100% of said IGF-1 from said eluate,
  (d) eluting the adsorbed IGF-1 from said first hydrophobic interaction chromatography matrix by contacting said matrix first with in the range of about 1 up to 10 volumes, relative to the volume of matrix, of a buffer system having a sufficiently low conductivity so as to displace aberrant IGF-1 peptides from said matrix, without displacing significant quantities of the intact, monomeric, correctly-folded form of adsorbed IGF-1 from said firs hydrophobic interaction chromatography matrix, followed by contacting said matrix with in the range of about 1 up to 10 volumes, relative to the volume of matrix, of a buffer system having an elevated pH, wherein said elevated pH is sufficiently high so as to displace substantially all of the remaining adsorbed forms of IGF-1 from said matrix.

40. A method according to claim 39 wherein prior to the elution in step (b) the IGF-1-containing cation exchange chromatography matrix is subjected to a step-wise wash system selected from the group consisting of: (1) (i) a dilute acetic acid solution followed by (ii) an acetate buffer solution having a pH of about 5 and having a concentration of about 0.2M salt; (2) (i) a dilute acetic acid solution followed by (ii) an acetate buffered solution having a pH of about 5, followed by (iii) an acetate buffered solution having a pH of about 5.5.

41. A method according to claim 39 wherein prior to the elution in step (b) the IGF-1-containing cation exchange chromatography matrix is subjected to a stepwise wash system selected from the group consisting of: (1) 20 mM acetic acid followed by 20 mM sodium acetate, pH 5, containing 0.2M NaCl or (2) 20 mM acetic acid followed by 50 mM sodium acetate, pH 5, followed by 50 mM sodium acetate, pH 5.5.

42. A method according to claim 39 wherein prior to the elution in step (b) the IGF-1-containing cation exchange chromatography matrix is subjected to a stepwise wash system consisting of: (1) a dilute acetic acid solution; (2) a salt-free acetate buffer solution having a pH of about 5.5; (3) an acetate buffer solution having a pH of about 5.5 and having about 0.05M salt; and (4) an acetate buffer solution having a pH of about 5.5 and having about 0.1M salt.

43. A method according to claim 42 wherein the step-wise wash system consists of 20 mM acetic acid followed by 50 mM sodium acetate, pH 5.5, followed by 0.05M NaCl in 50 mM sodium acetate, pH 5.5, followed by 0.1M NaCl in 50 mM sodium acetate, pH 5.5.

44. A method according to claim 42 wherein the solvent system of step (b) is an acetate buffer solution having a pH of about 5.5 and having about 0.3M salt.

45. A method according to claim 43 wherein the solvent system of step (b) is 0.3M NaCl, 50 mM sodium acetate, pH 5.5.

46. A method according to claim 39 wherein the solvent system in step (b) is a linear salt gradient starting with a substantially salt-free buffer solution having a pH of about 5.5 and ending with a buffer solution having substantially the same pH and having a salt concentration of about 0.5M.

47. A method according to claim 46 wherein the salt is sodium chloride.

48. A method according to claim 39 wherein the buffer system having a sufficiently low conductivity is a linear gradient starting at 20% saturated ammonium sulfate buffered at pH 4.5 with 50 mM sodium acetate/phosphate, and ending with 0% ammonium sulfate buffered at pH 4.5 with the same buffer.

49. A method according to claim 48 wherein the buffer system having an elevated pH is an increasing pH gradient starting at a pH of about 4.5 and ending at a pH of about 6.5.

50. A method according to claim 39 wherein the buffer system having a sufficiently low conductivity is a linear gradient starting at 20% saturated ammonium sulfate buffered at pH 5.0 with 50 mM sodium acetate/phosphate, and ending with 0% ammonium sulfate buffered at pH 4.0 with the same buffer.

51. A method according to claim 50 wherein after the linear gradient, the hydrophobic interaction chromatography matrix is further contacted with an ammonium sulfate-free solution buffered at pH 4.0.

52. A method according to claim 51 wherein the buffer system having an elevated pH is a solution having a pH in the range of 6.5 to 7.5.

53. A method according to claim 39, said method further comprising:
  (e) after step (d), contacting the intact, monomeric, correctly-folded IGF-1-containing fractions of the eluate from step (d), in a suitable solvent system, with a sufficient quantity of a gel filtration chromatography matrix having suitable pore size to effect resolution of the intact, monomeric correctly-folded form of IGF-1 from substantially all multimeric forms of IGF-1; and (f) eluting said gel filtration chromatography matrix with a sufficient quantity of an eluent so as to cause the intact, monomeric correctly-folded form of IGF-1 to be resolved from said multimeric forms of IGF-1.

54. A method according to claim 53 wherein said eluent is a solution having a concentration of about 50 mM ammonium acetate and a pH of about 6.0.

55. A method according to claim 53 wherein the gel filtration chromatography matrix is a polymer-based resin, and the eluent in step (f) is an acetic acid solution.

56. A method according to claim 55 wherein the gel filtration chromatography matrix is Toyopearl HW50F and the eluent is an acetic acid solution having a concentration of about 0.2M.

* * * * *